US008304202B2

(12) United States Patent
Meller

(10) Patent No.: US 8,304,202 B2
(45) Date of Patent: Nov. 6, 2012

(54) INTERACTION OF BIM WITH TRIM2

(75) Inventor: Robert Meller, Portland, OR (US)

(73) Assignee: Legacy Emanuel Hospital & Health Center, Portland, OR (US)

( * ) Notice: Subject to any disclaimer, the term of this patent is extended or adjusted under 35 U.S.C. 154(b) by 210 days.

(21) Appl. No.: 12/697,097

(22) Filed: Jan. 29, 2010

(65) Prior Publication Data
US 2010/0203552 A1 Aug. 12, 2010

Related U.S. Application Data

(63) Continuation-in-part of application No. 12/178,491, filed on Jul. 23, 2008, now abandoned.

(60) Provisional application No. 60/961,848, filed on Jul. 23, 2007.

(51) Int. Cl.
*G01N 33/53* (2006.01)
(52) U.S. Cl. .................................. 435/7.23
(58) Field of Classification Search .................. None
See application file for complete search history.

(56) References Cited

OTHER PUBLICATIONS

Gura (Science, 1997, 278:1041-1042).*
Jain (Sci. Am., 1994, 271:58-65).*
Akiyama et al., Regulation of Osteoclast Apoptosis by Ubiquitylation of Proapoptotic BH3-only Bcl-2 Family Member Bim, The Embo Journal, Dec. 15, 2003, pp. 6653-6664, vol. 22, Issue 24, Nature Publishing Group, Germany.
Kuan, et al., A Critical Role of Neural-Specific JNK3 for Ischemic Apoptosis, Proceedings of The National Academy of Sciences of the United States of America, Dec. 9, 2003, pp. 15184-15189, vol. 100, Issue 25, National Academy of Sciences, Washington, D.C.
Ohkawa,et al., Molecular Cloning and Characterization of Neural Activity-Related RING Finger Protein (NARF): a New Member of the RBCC Family is a Candidate for the Partner of Myosin V, The Journal of Neurochemistry, Jul. 2001, pp. 75-87, vol. 78, Issue 1, Wiley-Blackwell.
Reymond,et al., The Tripartite Motif Family Identifies Cell Compartments, The Embo Journal, May 1, 2001, pp. 2140-2151, vol. 20, Issue 9, Nature Publishing Group, Germany.
Meroni, et al., TRIM/RBCC, a Novel Class of 'Single Protein RING Finger' E3 Ubiquitin Ligases, BioEssays, Nov. 2005, pp. 1147-1157, vol. 27, Issue 11, Wiley Periodicals, Inc.
Miyatake, et al., Down-Regulation of Insulin-Like Growth Factor Binding Protein-5 (IGFBP-5):Novel Marker for Cervical Carcinogenesis, International Journal of Cancer, May 15, 2007, pp. 2068-2077, vol. 120, Issue 10, Wiley-Liss, Inc.
Nisole, et al., Trim Family Proteins: Retroviral Restriction and Antiviral Defence, Nature Reviews Microbiology, Oct. 1, 2005, pp. 799-808, vol. 3, Issue 10, Nature Publishing Group, Germany.
Diepen, et al., The Molluscan RING-Finger Protein L-TRIM is Essential for Neuronal Outgrowth, Department of Molecular and Cellular Neuroscience, May 3, 2005, pp. 74-81, vol. 29, Issue 1, Institute of Neuroscience, The Netherlands.

Meller, et al., Rapid Degradation of Bim by the Ubiquitin-Proteasome Pathway Mediates Short-term Ischemic Tolerance in Cultured Neurons, The Journal of Biological Chemistry, Mar. 17, 2006, pp. 7429-7436, vol. 281, Issue 11, The American Society fro Biochemical and Molecular Biology, Rockville, Maryland.
Nguyen, et al., Evolutionary Optimization of Fluorescent Proteins for Intracellular FRET, Nature Biotechnology, Mar. 2005, pp. 267-394, vol. 23, Issue 3, Nature Publishing Group, Germany.
Ley, et al., Activation of the ERK1/2 Signaling Pathway Promotes Phosphorylation and Proteasome-dependent Degradation of the BH3-only Protein, Bim, The Journal of Biological Chemistry, May 23, 2003, pp. 18811-18816, vol. 278, Issue 21, The American Society for Biochemical and Molecular Biology, Rockville, Maryland.
Ley, et al., Regulatory Phosphorylation of Bim: Sorting Out the ERK from the JNK, Cell Death and Differentiation, Aug. 2005, pp. 1008-1014, vol. 12, Issue 8, The Nature Publishing Group, Germany.
Ley, et al., Extracellular Signal-Regulated Kinases 1/2 are Serum-Stimulated "Bim(EL) Kinases" that Bind to the BH3-only Protein Bim(EL) Causing its Phosphorylation and Turnover, The Journal of Biological Chemistry, Mar. 5, 2004, pp. 8837-8847, vol. 279, Issue 10, The American Society for Biochemical and Molecular Biology, Rockville, Maryland.
Ley, et al., Identification of a DEF-type Docking Domain for Extracellular Signal-regulated Kinases 1/2 That Directs Phosphorylation and Turnover of the BH3-only Protein BimEL, The Journal of Biological Chemistry, May 6, 2005, pp. 17657-17663, vol. 280, Issue 18, The American Society for Biochemical and Molecular Biology, Rockville, Maryland.
Wiggins, et al., c-Cbl is Not Required for ERK1/2-Dependent Degradation of BimEL, Laboratory of Molecular Signalling, Dec. 19, 2007, pp. 2605-2611, vol. 19, Issue 12, The Babraham Institute, United Kingdom.
Zhang, et al., RACK1 and CIS Mediate the Degradation of BimEL in Cancer Cells, The Journal of Biological Chemistry, Jun. 13, 2008, pp. 16416-16426, vol. 283, Issue 24, The American Society for Biochemical and Molecular Biology, Rockville, Maryland.
Putcha, et al., JNK-Mediated BIM Phosphorylation Potentiates BAX-Dependent Apoptosis, Neuron, Jun. 19, 2003, vol. 38, Issue 6, Cell Press, Inc. Cambridge, MA.
Qi, et al., Evidence That Ser87 of BimEL Is Phosphorylated by Akt and Regulates BimEL Apoptotic Function, The Journal of Biological Chemistry, Jan. 13, 2006, pp. 813-823, vol. 281, Issue 2, The American Society for Biochemical and Molecular Biology, Rockville, Maryland.
Meller, et al., CREB-mediated Bcl-2 Protein Expression after Ischemic Preconditioning,The Journal of Cerebral Blood Flow and Metabolism, Feb. 2005, pp. 234-246, vol. 25, Issue 2, The Nature Publishing Group, Germany.
Wiggins, et al., Refining the Minimal Sequence Required for ERK1/2-dependent Poly-Ubiquitination and Proteasome-Dependent Turnover of BIM, Laboratory of Molecular Signalling, Jan. 13, 2010 pp. 801-808, vol. 22, Issue 5, The Babraham Institute, United Kingdom.
Balastik, et al., Deficiency in Ubiquitin Ligase TRIM2 Causes Accumulation of Neurofilament Light Chain and Neurodegeneration, Proceedings of The National Academy of Sciences of the United States of America, Aug. 19, 2008, pp. 12016-12021, vol. 105, Issue 33, National Academy of Sciences, Washington, D.C.

* cited by examiner

*Primary Examiner* — Sheela J Huff
(74) *Attorney, Agent, or Firm* — Kolisch Hartwell, P.C.

(57) ABSTRACT

Methods, compositions, and cells for drug screening based on interaction between a Bim polypeptide and a TRIM2 polypeptide. Methods and compositions for treating cancer based on tested levels of Bim and TRIM2 proteins are also provided.

14 Claims, 9 Drawing Sheets

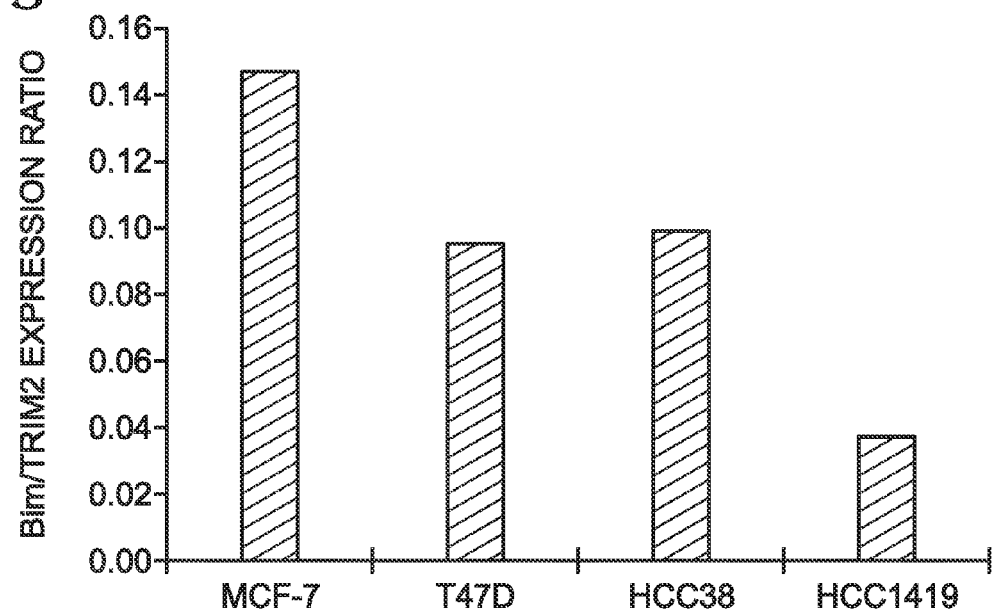
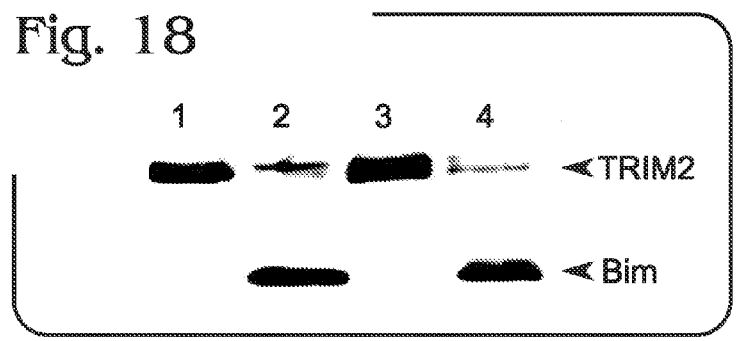

SEQUENCE LISTING

```
<160> NUMBER OF SEQ ID NOS: 12

<210> SEQ ID NO 1
<211> LENGTH: 198
<212> TYPE: PRT
<213> ORGANISM: Homo sapiens
<300> PUBLICATION INFORMATION:
<308> DATABASE ACCESSION NUMBER: GenBank AAC39593
<309> DATABASE ENTRY DATE: 1998-02-19
<313> RELEVANT RESIDUES IN SEQ ID NO: (1)..(198)

<400> SEQUENCE: 1
```

```
Met Ala Lys Gln Pro Ser Asp Val Ser Ser Glu Cys Asp Arg Glu Gly
1               5                   10                  15

Arg Gln Leu Gln Pro Ala Glu Arg Pro Pro Gln Leu Arg Pro Gly Ala
                20                  25                  30

Pro Thr Ser Leu Gln Thr Glu Pro Gln Gly Asn Pro Gly Asn His
            35                  40                  45

Gly Gly Glu Gly Asp Ser Cys Pro His Gly Ser Pro Gln Gly Pro Leu
    50                  55                  60

Ala Pro Pro Ala Ser Pro Gly Pro Phe Ala Thr Arg Ser Pro Leu Phe
65              70                  75                      80

Ile Phe Met Arg Arg Ser Ser Leu Leu Ser Arg Ser Ser Ser Gly Tyr
                    85                  90                  95

Phe Ser Phe Asp Thr Asp Arg Ser Pro Ala Pro Met Ser Cys Asp Lys
                100                 105                 110

Ser Thr Gln Thr Pro Ser Pro Pro Cys Gln Ala Phe Asn His Tyr Leu
            115                 120                 125

Ser Ala Met Ala Ser Met Arg Gln Ala Glu Pro Ala Asp Met Arg Pro
    130                 135                 140

Glu Ile Trp Ile Ala Gln Leu Arg Arg Ile Gly Asp Glu Phe Asn
145                 150                 155                 160

Ala Tyr Tyr Ala Arg Arg Val Phe Leu Asn Asn Tyr Gln Ala Ala Glu
                165                 170                 175

Asp His Pro Arg Met Val Ile Leu Arg Leu Leu Arg Tyr Ile Val Arg
            180                 185                 190

Leu Val Trp Arg Met His
            195

<210> SEQ ID NO 2
<211> LENGTH: 196
<212> TYPE: PRT
<213> ORGANISM: Mus musculus
<300> PUBLICATION INFORMATION:
<308> DATABASE ACCESSION NUMBER: GenBank AAC40029
<309> DATABASE ENTRY DATE: 1998-02-19
<313> RELEVANT RESIDUES IN SEQ ID NO: (1)..(196)

<400> SEQUENCE: 2

Met Ala Lys Gln Pro Ser Asp Val Ser Ser Glu Cys Asp Arg Glu Gly
1               5                   10                  15

Gly Gln Leu Gln Pro Ala Glu Arg Pro Pro Gln Leu Arg Pro Gly Ala
                20                  25                  30

Pro Thr Ser Leu Gln Thr Glu Pro Gln Gly Asn Pro Asp Gly Glu Gly
            35                  40                  45

Asp Arg Cys Pro His Gly Ser Pro Gln Gly Pro Leu Ala Pro Ala
    50                  55                  60

Ser Pro Gly Pro Phe Ala Thr Arg Ser Pro Leu Phe Ile Phe Val Arg
65              70                  75                      80

Arg Ser Ser Leu Leu Ser Arg Ser Ser Ser Gly Tyr Phe Ser Phe Asp
                    85                  90                  95

Thr Asp Arg Ser Pro Ala Pro Met Ser Cys Asp Lys Ser Thr Gln Thr
                100                 105                 110

Pro Ser Pro Pro Cys Gln Ala Phe Asn His Tyr Leu Ser Ala Met Ala
            115                 120                 125

Ser Ile Arg Gln Ser Gln Glu Glu Pro Glu Asp Leu Arg Pro Glu Ile
    130                 135                 140

Arg Ile Ala Gln Glu Leu Arg Arg Ile Gly Asp Glu Phe Asn Glu Thr
```

```
                145                 150                 155                 160
Tyr Thr Arg Arg Val Phe Ala Asn Asp Tyr Arg Glu Ala Glu Asp His
                    165                 170                 175

Pro Gln Met Val Ile Leu Gln Leu Leu Arg Phe Ile Phe Arg Leu Val
            180                 185                 190

Trp Arg Arg His
        195

<210> SEQ ID NO 3
<211> LENGTH: 196
<212> TYPE: PRT
<213> ORGANISM: Rattus norvegicus
<300> PUBLICATION INFORMATION:
<308> DATABASE ACCESSION NUMBER: NCBI NP_741985
<309> DATABASE ENTRY DATE: 2010-01-26
<313> RELEVANT RESIDUES IN SEQ ID NO: (1)..(196)

<400> SEQUENCE: 3

Met Ala Lys Gln Pro Ser Asp Val Asn Ser Glu Cys Asp Arg Glu Gly
1               5                   10                  15

Gly Gln Leu Gln Pro Ala Glu Arg Pro Pro Gln Leu Arg Pro Gly Ala
            20                  25                  30

Pro Thr Ser Leu Gln Thr Glu Ser Gln Gly Asn Pro Asp Gly Glu Gly
        35                  40                  45

Asp Arg Cys Pro His Gly Ser Pro Gln Gly Pro Leu Ala Pro Pro Ala
    50                  55                  60

Ser Pro Gly Pro Phe Ala Thr Arg Ser Pro Leu Phe Ile Phe Val Arg
65                  70                  75                  80

Arg Ser Ser Leu Leu Ser Arg Ser Ser Ser Gly Tyr Phe Ser Phe Asp
                85                  90                  95

Thr Asp Arg Ser Pro Ala Pro Met Ser Cys Asp Lys Ser Thr Gln Thr
            100                 105                 110

Pro Ser Pro Pro Cys Gln Ala Phe Asn His Tyr Leu Ser Ala Met Ala
        115                 120                 125

Ser Ile Arg Gln Ser Gln Glu Glu Pro Glu Asp Leu Arg Pro Glu Ile
    130                 135                 140

Arg Ile Ala Gln Glu Leu Arg Arg Ile Gly Asp Glu Phe Asn Glu Thr
145                 150                 155                 160

Tyr Thr Arg Arg Ala Phe Ala Asn Asp Tyr Arg Glu Ala Glu Asp His
                165                 170                 175

Pro Gln Met Val Ile Leu Gln Leu Leu Arg Phe Ile Phe Arg Leu Val
            180                 185                 190

Trp Arg Arg His
        195

<210> SEQ ID NO 4
<211> LENGTH: 196
<212> TYPE: PRT
<213> ORGANISM: Equus caballus
<300> PUBLICATION INFORMATION:
<308> DATABASE ACCESSION NUMBER: NCBI XP_001495305
<309> DATABASE ENTRY DATE: 2008-07-11
<313> RELEVANT RESIDUES IN SEQ ID NO: (1)..(196)

<400> SEQUENCE: 4

Met Ala Lys Gln Pro Ser Asp Val Ser Ser Glu Cys Asp Arg Glu Gly
1               5                   10                  15

Gly Gln Leu Gln Pro Ala Glu Arg Pro Pro Gln Leu Arg Pro Gly Ala
            20                  25                  30
```

```
Pro Thr Ser Leu Gln Ile Glu Gln Gln Gly Asn Pro Gly Gly Gly
            35                  40                  45

Asp Arg Cys Pro Gln Gly Ser Pro Leu Gly Pro Leu Ala Pro Ala
 50                  55                  60

Ser Pro Gly Pro Phe Ala Thr Arg Ser Pro Phe Phe Ile Phe Val Arg
 65                  70                  75                  80

Arg Ser Ser Leu Leu Ser Arg Ser Ser Gly Tyr Phe Ser Phe Asp
                 85                  90                  95

Thr Asp Arg Ser Pro Ala Pro Met Ser Cys Asp Lys Ser Thr Gln Thr
                100                 105                 110

Pro Ser Pro Pro Cys Gln Ala Phe Asn His Tyr Leu Ser Ala Met Ala
            115                 120                 125

Ser Met Arg Gln Ser Gln Ala Val Pro Ala Asp Met Arg Pro Glu Val
130                 135                 140

Trp Ile Ala Gln Glu Leu Arg Arg Ile Gly Asp Glu Phe Asn Ala Ser
145                 150                 155                 160

Tyr Pro Arg Arg Val Val Leu Asn His His Gln Ala Ala Glu Ala His
                165                 170                 175

Pro Gln Met Ile Ile Leu Arg Leu Leu Arg Tyr Ile Ile Arg Leu Val
            180                 185                 190

Arg Arg Leu Gln
        195

<210> SEQ ID NO 5
<211> LENGTH: 198
<212> TYPE: PRT
<213> ORGANISM: Macaca mulatta
<300> PUBLICATION INFORMATION:
<308> DATABASE ACCESSION NUMBER: NCBI XP_001086237
<309> DATABASE ENTRY DATE: 2006-06-14
<313> RELEVANT RESIDUES IN SEQ ID NO: (1)..(198)

<400> SEQUENCE: 5

Met Ala Lys Gln Pro Ser Asp Val Ser Ser Glu Cys Asp Arg Glu Gly
 1               5                  10                  15

Arg Gln Leu Gln Pro Ala Glu Arg Pro Pro Gln Leu Arg Pro Gly Ala
                20                  25                  30

Pro Thr Ser Leu Gln Thr Glu Pro Gln Gly Asn Pro Glu Gly Asn His
            35                  40                  45

Gly Gly Glu Gly Asp Ser Cys Pro His Gly Ser Pro Gln Gly Pro Leu
 50                  55                  60

Ala Pro Pro Ala Ser Pro Gly Pro Phe Ala Thr Arg Ser Pro Leu Phe
 65                  70                  75                  80

Ile Phe Met Arg Arg Ser Ser Leu Leu Ser Arg Ser Ser Ser Gly Tyr
                 85                  90                  95

Phe Ser Phe Asp Thr Asp Arg Ser Pro Ala Pro Met Ser Cys Asp Lys
                100                 105                 110

Ser Thr Gln Thr Pro Ser Pro Pro Cys Gln Ala Phe Asn His Tyr Leu
            115                 120                 125

Ser Ala Met Ala Ser Arg Arg Gln Ala Glu Pro Ala Asp Met Arg Pro
130                 135                 140

Glu Ile Arg Ile Ala Gln Glu Leu Arg Arg Ile Gly Asp Glu Phe Asn
145                 150                 155                 160

Ala Tyr Tyr Ala Arg Arg Val Phe Leu Asn Asn Tyr Gln Ala Ala Glu
                165                 170                 175

Asn His Pro Gln Met Val Ile Leu Arg Leu Leu Arg Tyr Ile Val Arg
            180                 185                 190
```

Leu Val Trp Arg Met His
        195

<210> SEQ ID NO 6
<211> LENGTH: 770
<212> TYPE: PRT
<213> ORGANISM: Homo sapiens
<300> PUBLICATION INFORMATION:
<308> DATABASE ACCESSION NUMBER: GenBank EAX04963
<309> DATABASE ENTRY DATE: 2006-12-18
<313> RELEVANT RESIDUES IN SEQ ID NO: (1)..(770)

<400> SEQUENCE: 6

Met His Arg Ser Gly Arg Tyr Gly Thr Gln Gln Arg Ala Gly Ser Lys
1               5                   10                  15

Thr Ala Gly Pro Pro Cys Gln Trp Ser Arg Met Ala Ser Glu Gly Thr
            20                  25                  30

Asn Ile Pro Ser Pro Val Val Arg Gln Ile Asp Lys Gln Phe Leu Ile
        35                  40                  45

Cys Ser Ile Cys Leu Glu Arg Tyr Lys Asn Pro Lys Val Leu Pro Cys
    50                  55                  60

Leu His Thr Phe Cys Glu Arg Cys Leu Gln Asn Tyr Ile Pro Ala His
65                  70                  75                  80

Ser Leu Thr Leu Ser Cys Pro Val Cys Arg Gln Thr Ser Ile Leu Pro
                85                  90                  95

Glu Lys Gly Val Ala Ala Leu Gln Asn Asn Phe Phe Ile Thr Asn Leu
            100                 105                 110

Met Asp Val Leu Gln Arg Thr Pro Gly Ser Asn Ala Glu Glu Ser Ser
        115                 120                 125

Ile Leu Glu Thr Val Thr Ala Val Ala Ala Gly Lys Pro Leu Ser Cys
    130                 135                 140

Pro Asn His Asp Gly Asn Val Met Glu Phe Tyr Cys Gln Ser Cys Glu
145                 150                 155                 160

Thr Ala Met Cys Arg Glu Cys Thr Glu Gly Glu His Ala Glu His Pro
                165                 170                 175

Thr Val Pro Leu Lys Asp Val Val Glu Gln His Lys Ala Ser Leu Gln
            180                 185                 190

Val Gln Leu Asp Ala Val Asn Lys Arg Leu Pro Glu Ile Asp Ser Ala
        195                 200                 205

Leu Gln Phe Ile Ser Glu Ile Ile His Gln Leu Thr Asn Gln Lys Ala
    210                 215                 220

Ser Ile Val Asp Asp Ile His Ser Thr Phe Asp Glu Leu Gln Lys Thr
225                 230                 235                 240

Leu Asn Val Arg Lys Ser Val Leu Leu Met Glu Leu Glu Val Asn Tyr
                245                 250                 255

Gly Leu Lys His Lys Val Leu Gln Ser Gln Leu Asp Thr Leu Leu Gln
            260                 265                 270

Gly Gln Glu Ser Ile Lys Ser Cys Ser Asn Phe Thr Ala Gln Ala Leu
        275                 280                 285

Asn His Gly Thr Glu Thr Glu Val Leu Leu Val Lys Lys Gln Met Ser
    290                 295                 300

Glu Lys Leu Asn Glu Leu Ala Asp Gln Asp Phe Pro Leu His Pro Arg
305                 310                 315                 320

Glu Asn Asp Gln Leu Asp Phe Ile Val Glu Thr Glu Gly Leu Lys Lys
                325                 330                 335

Ser Ile His Asn Leu Gly Thr Ile Leu Thr Thr Asn Ala Val Ala Ser

```
                    340                 345                 350
Glu Thr Val Ala Thr Gly Glu Gly Leu Arg Gln Thr Ile Ile Gly Gln
            355                 360                 365

Pro Met Ser Val Thr Ile Thr Thr Lys Asp Lys Asp Gly Glu Leu Cys
    370                 375                 380

Lys Thr Gly Asn Ala Tyr Leu Thr Ala Glu Leu Ser Thr Pro Asp Gly
385                 390                 395                 400

Ser Val Ala Asp Gly Glu Ile Leu Asp Asn Lys Asn Gly Thr Tyr Glu
                405                 410                 415

Phe Leu Tyr Thr Val Gln Lys Glu Gly Asp Phe Thr Leu Ser Leu Arg
            420                 425                 430

Leu Tyr Asp Gln His Ile Arg Gly Ser Pro Phe Lys Leu Lys Val Ile
        435                 440                 445

Arg Ser Ala Asp Val Ser Pro Thr Glu Gly Val Lys Arg Arg Val
    450                 455                 460

Lys Ser Pro Gly Ser Gly His Val Lys Gln Lys Ala Val Lys Arg Pro
465                 470                 475                 480

Ala Ser Met Tyr Ser Thr Gly Lys Arg Lys Glu Asn Pro Ile Glu Asp
                485                 490                 495

Asp Leu Ile Phe Arg Val Gly Thr Lys Gly Arg Asn Lys Gly Glu Phe
            500                 505                 510

Thr Asn Leu Gln Gly Val Ala Ala Ser Thr Asn Gly Lys Ile Leu Ile
        515                 520                 525

Ala Asp Ser Asn Gln Cys Val Gln Ile Phe Ser Asn Asp Gly Gln
    530                 535                 540

Phe Lys Ser Arg Phe Gly Ile Arg Gly Arg Ser Pro Gly Gln Leu Gln
545                 550                 555                 560

Arg Pro Thr Gly Val Ala Val His Pro Ser Gly Asp Ile Ile Ala
                565                 570                 575

Asp Tyr Asp Asn Lys Trp Val Ser Ile Phe Ser Ser Gly Lys Phe
            580                 585                 590

Lys Thr Lys Ile Gly Ser Gly Lys Leu Met Gly Pro Lys Gly Val Ser
        595                 600                 605

Val Asp Arg Asn Gly His Ile Ile Val Val Asp Asn Lys Ala Cys Cys
    610                 615                 620

Val Phe Ile Phe Gln Pro Asn Gly Lys Ile Val Thr Arg Phe Gly Ser
625                 630                 635                 640

Arg Gly Asn Gly Asp Arg Gln Phe Ala Gly Pro His Phe Ala Ala Val
                645                 650                 655

Asn Ser Asn Asn Glu Ile Ile Ile Thr Asp Phe His Asn His Ser Val
            660                 665                 670

Lys Val Phe Asn Gln Glu Gly Glu Phe Met Leu Lys Phe Gly Ser Asn
        675                 680                 685

Gly Glu Gly Asn Gly Gln Phe Asn Ala Pro Thr Gly Val Ala Val Asp
    690                 695                 700

Ser Asn Gly Asn Ile Ile Val Ala Asp Trp Gly Asn Ser Arg Ile Gln
705                 710                 715                 720

Val Phe Asp Gly Ser Gly Ser Phe Leu Ser Tyr Ile Asn Thr Ser Ala
                725                 730                 735

Asp Pro Leu Tyr Gly Pro Gln Gly Leu Ala Leu Thr Ser Asp Gly His
            740                 745                 750

Val Val Val Ala Asp Ser Gly Asn His Cys Phe Lys Val Tyr Arg Tyr
        755                 760                 765
```

-continued

Leu Gln
    770

<210> SEQ ID NO 7
<211> LENGTH: 744
<212> TYPE: PRT
<213> ORGANISM: Homo sapiens
<300> PUBLICATION INFORMATION:
<308> DATABASE ACCESSION NUMBER: NCBI NP_001123539
<309> DATABASE ENTRY DATE: 2009-09-03
<313> RELEVANT RESIDUES IN SEQ ID NO: (1)..(744)

<400> SEQUENCE: 7

```
Met Ala Ser Glu Gly Thr Asn Ile Pro Ser Pro Val Val Arg Gln Ile
1               5                   10                  15

Asp Lys Gln Phe Leu Ile Cys Ser Ile Cys Leu Glu Arg Tyr Lys Asn
            20                  25                  30

Pro Lys Val Leu Pro Cys Leu His Thr Phe Cys Glu Arg Cys Leu Gln
        35                  40                  45

Asn Tyr Ile Pro Ala His Ser Leu Thr Leu Ser Cys Pro Val Cys Arg
    50                  55                  60

Gln Thr Ser Ile Leu Pro Glu Lys Gly Val Ala Ala Leu Gln Asn Asn
65                  70                  75                  80

Phe Phe Ile Thr Asn Leu Met Asp Val Leu Gln Arg Thr Pro Gly Ser
                85                  90                  95

Asn Ala Glu Glu Ser Ser Ile Leu Glu Thr Val Thr Ala Val Ala Ala
            100                 105                 110

Gly Lys Pro Leu Ser Cys Pro Asn His Asp Gly Asn Val Met Glu Phe
        115                 120                 125

Tyr Cys Gln Ser Cys Glu Thr Ala Met Cys Arg Glu Cys Thr Glu Gly
    130                 135                 140

Glu His Ala Glu His Pro Thr Val Pro Leu Lys Asp Val Val Glu Gln
145                 150                 155                 160

His Lys Ala Ser Leu Gln Val Gln Leu Asp Ala Val Asn Lys Arg Leu
                165                 170                 175

Pro Glu Ile Asp Ser Ala Leu Gln Phe Ile Ser Glu Ile Ile His Gln
            180                 185                 190

Leu Thr Asn Gln Lys Ala Ser Ile Val Asp Asp Ile His Ser Thr Phe
        195                 200                 205

Asp Glu Leu Gln Lys Thr Leu Asn Val Arg Lys Ser Val Leu Leu Met
    210                 215                 220

Glu Leu Glu Val Asn Tyr Gly Leu Lys His Lys Val Leu Gln Ser Gln
225                 230                 235                 240

Leu Asp Thr Leu Leu Gln Gly Gln Glu Ser Ile Lys Ser Cys Ser Asn
                245                 250                 255

Phe Thr Ala Gln Ala Leu Asn His Gly Thr Glu Thr Glu Val Leu Leu
            260                 265                 270

Val Lys Lys Gln Met Ser Glu Lys Leu Asn Glu Leu Ala Asp Gln Asp
        275                 280                 285

Phe Pro Leu His Pro Arg Glu Asn Asp Gln Leu Asp Phe Ile Val Glu
    290                 295                 300

Thr Glu Gly Leu Lys Lys Ser Ile His Asn Leu Gly Thr Ile Leu Thr
305                 310                 315                 320

Thr Asn Ala Val Ala Ser Glu Thr Val Ala Thr Gly Glu Gly Leu Arg
                325                 330                 335

Gln Thr Ile Ile Gly Gln Pro Met Ser Val Thr Ile Thr Thr Lys Asp
            340                 345                 350
```

Lys Asp Gly Glu Leu Cys Lys Thr Gly Asn Ala Tyr Leu Thr Ala Glu
            355                 360                 365

Leu Ser Thr Pro Asp Gly Ser Val Ala Asp Gly Glu Ile Leu Asp Asn
        370                 375                 380

Lys Asn Gly Thr Tyr Glu Phe Leu Tyr Thr Val Gln Lys Glu Gly Asp
385                 390                 395                 400

Phe Thr Leu Ser Leu Arg Leu Tyr Asp Gln His Ile Arg Gly Ser Pro
                405                 410                 415

Phe Lys Leu Lys Val Ile Arg Ser Ala Asp Val Ser Pro Thr Thr Glu
            420                 425                 430

Gly Val Lys Arg Arg Val Lys Ser Pro Gly Ser Gly His Val Lys Gln
        435                 440                 445

Lys Ala Val Lys Arg Pro Ala Ser Met Tyr Ser Thr Gly Lys Arg Lys
    450                 455                 460

Glu Asn Pro Ile Glu Asp Asp Leu Ile Phe Arg Val Gly Thr Lys Gly
465                 470                 475                 480

Arg Asn Lys Gly Glu Phe Thr Asn Leu Gln Gly Val Ala Ala Ser Thr
                485                 490                 495

Asn Gly Lys Ile Leu Ile Ala Asp Ser Asn Asn Gln Cys Val Gln Ile
            500                 505                 510

Phe Ser Asn Asp Gly Gln Phe Lys Ser Arg Phe Gly Ile Arg Gly Arg
        515                 520                 525

Ser Pro Gly Gln Leu Gln Arg Pro Thr Gly Val Ala Val His Pro Ser
    530                 535                 540

Gly Asp Ile Ile Ile Ala Asp Tyr Asp Asn Lys Trp Val Ser Ile Phe
545                 550                 555                 560

Ser Ser Asp Gly Lys Phe Lys Thr Lys Ile Gly Ser Gly Lys Leu Met
                565                 570                 575

Gly Pro Lys Gly Val Ser Val Asp Arg Asn Gly His Ile Ile Val Val
            580                 585                 590

Asp Asn Lys Ala Cys Cys Val Phe Ile Phe Gln Pro Asn Gly Lys Ile
        595                 600                 605

Val Thr Arg Phe Gly Ser Arg Gly Asn Gly Asp Arg Gln Phe Ala Gly
    610                 615                 620

Pro His Phe Ala Ala Val Asn Ser Asn Asn Glu Ile Ile Ile Thr Asp
625                 630                 635                 640

Phe His Asn His Ser Val Lys Val Phe Asn Gln Glu Gly Glu Phe Met
                645                 650                 655

Leu Lys Phe Gly Ser Asn Gly Glu Gly Asn Gly Gln Phe Asn Ala Pro
            660                 665                 670

Thr Gly Val Ala Val Asp Ser Asn Gly Asn Ile Ile Val Ala Asp Trp
        675                 680                 685

Gly Asn Ser Arg Ile Gln Val Phe Asp Gly Ser Gly Ser Phe Leu Ser
    690                 695                 700

Tyr Ile Asn Thr Ser Ala Asp Pro Leu Tyr Gly Pro Gln Gly Leu Ala
705                 710                 715                 720

Leu Thr Ser Asp Gly His Val Val Ala Asp Ser Gly Asn His Cys
                725                 730                 735

Phe Lys Val Tyr Arg Tyr Leu Gln
            740

<210> SEQ ID NO 8
<211> LENGTH: 770
<212> TYPE: PRT

-continued

```
<213> ORGANISM: Mus musculus
<300> PUBLICATION INFORMATION:
<308> DATABASE ACCESSION NUMBER: GenBank BAE24679
<309> DATABASE ENTRY DATE: 2008-09-19
<313> RELEVANT RESIDUES IN SEQ ID NO: (1)..(770)

<400> SEQUENCE: 8

Met Pro Arg Ser Gly Arg Tyr Gly Thr Gln Gln Arg Ala Gly Ser Arg
1               5                   10                  15

Thr Ala Gly Pro Pro Cys Gln Trp Ser Arg Met Ala Ser Glu Gly Ala
            20                  25                  30

Ser Ile Pro Ser Pro Val Val Arg Gln Ile Asp Lys Gln Phe Leu Ile
        35                  40                  45

Cys Ser Ile Cys Leu Glu Arg Tyr Lys Asn Pro Lys Val Leu Pro Cys
    50                  55                  60

Leu His Thr Phe Cys Glu Arg Cys Leu Gln Asn Tyr Ile Pro Ala His
65                  70                  75                  80

Ser Leu Thr Leu Ser Cys Pro Val Cys Arg Gln Thr Ser Ile Leu Pro
                85                  90                  95

Glu Lys Gly Val Ala Ala Leu Gln Asn Asn Phe Phe Ile Thr Asn Leu
            100                 105                 110

Met Asp Val Leu Gln Arg Thr Pro Gly Ser Asn Gly Glu Asp Ser Ser
        115                 120                 125

Ile Leu Glu Thr Val Thr Ala Val Ala Ala Gly Lys Pro Leu Ser Cys
    130                 135                 140

Pro Asn His Asp Gly Asn Val Met Glu Phe Tyr Cys Gln Ser Cys Glu
145                 150                 155                 160

Thr Ala Met Cys Arg Glu Cys Thr Glu Gly Glu His Ala Glu His Pro
                165                 170                 175

Thr Val Pro Leu Lys Asp Val Val Glu Gln His Lys Ala Ser Leu Gln
            180                 185                 190

Val Gln Leu Asp Ala Val Asn Lys Arg Leu Pro Glu Ile Asp Ser Ala
        195                 200                 205

Leu Gln Phe Ile Ser Glu Ile Ile His Gln Leu Thr Asn Gln Lys Ala
    210                 215                 220

Ser Ile Val Asp Asp Ile His Ser Thr Phe Asp Glu Leu Gln Lys Thr
225                 230                 235                 240

Leu Asn Val Arg Lys Ser Met Leu Leu Met Glu Leu Glu Val Asn Tyr
                245                 250                 255

Gly Leu Lys His Lys Val Leu Gln Ser Gln Leu Asp Thr Leu Leu Gln
            260                 265                 270

Gly Gln Glu Ser Ile Lys Ser Cys Ser Asn Phe Thr Ala Gln Ala Leu
        275                 280                 285

Asn His Gly Thr Glu Thr Glu Val Leu Leu Val Lys Lys Gln Met Ser
    290                 295                 300

Glu Lys Leu Asn Glu Leu Ala Asp Gln Asp Phe Pro Leu His Pro Arg
305                 310                 315                 320

Glu Asn Asp Gln Leu Asp Phe Ile Val Glu Thr Glu Gly Leu Lys Lys
                325                 330                 335

Ser Ile His Asn Leu Gly Thr Ile Leu Thr Thr Asn Ala Val Ala Ser
            340                 345                 350

Glu Thr Val Ala Thr Gly Glu Gly Leu Arg Gln Thr Ile Ile Gly Gln
        355                 360                 365

Pro Met Ser Val Thr Ile Thr Thr Lys Asp Lys Asp Gly Glu Leu Cys
    370                 375                 380
```

```
Lys Thr Gly Asn Ala Tyr Leu Thr Ala Glu Leu Ser Thr Pro Asp Gly
385                 390                 395                 400

Ser Val Ala Asp Gly Glu Ile Leu Asp Asn Lys Asn Gly Thr Tyr Glu
            405                 410                 415

Phe Leu Tyr Thr Val Gln Lys Glu Gly Asp Phe Thr Leu Ser Leu Arg
        420                 425                 430

Leu Tyr Asp Gln His Ile Arg Gly Ser Pro Phe Lys Leu Lys Val Ile
    435                 440                 445

Arg Ser Ala Asp Val Ser Pro Thr Glu Gly Val Lys Arg Arg Val
450                 455                 460

Lys Ser Pro Gly Ser Gly His Val Lys Gln Lys Ala Val Lys Arg Pro
465                 470                 475                 480

Ala Ser Met Tyr Ser Thr Gly Lys Arg Lys Glu Asn Pro Ile Glu Asp
            485                 490                 495

Asp Leu Ile Phe Arg Val Gly Thr Lys Gly Arg Asn Lys Gly Glu Phe
        500                 505                 510

Thr Asn Leu Gln Gly Val Ala Ala Ser Thr Ser Gly Lys Ile Leu Ile
    515                 520                 525

Ala Asp Ser Asn Asn Gln Cys Val Gln Ile Phe Ser Asn Asp Gly Gln
530                 535                 540

Phe Lys Ser Arg Phe Gly Ile Arg Gly Arg Ser Pro Gly Gln Leu Gln
545                 550                 555                 560

Arg Pro Thr Gly Val Ala Val His Pro Ser Gly Asp Ile Ile Ala
            565                 570                 575

Asp Tyr Asp Asn Lys Trp Val Ser Ile Phe Ser Asn Asp Gly Lys Phe
        580                 585                 590

Lys Thr Lys Ile Gly Ser Gly Lys Leu Met Gly Pro Lys Gly Val Ser
    595                 600                 605

Val Asp Arg Asn Gly His Ile Ile Val Val Asp Asn Lys Ala Cys Cys
610                 615                 620

Val Phe Ile Phe Gln Pro Asn Gly Lys Ile Val Thr Arg Phe Gly Ser
625                 630                 635                 640

Arg Gly Asn Gly Asp Arg Gln Phe Ala Gly Pro His Phe Ala Ala Val
            645                 650                 655

Asn Ser Asn Asn Glu Ile Ile Ile Thr Asp Phe His Asn His Ser Val
        660                 665                 670

Lys Val Phe Asn Gln Glu Gly Glu Phe Met Leu Lys Phe Gly Ser Asn
    675                 680                 685

Gly Glu Gly Asn Gly Gln Phe Asn Ala Pro Thr Gly Val Ala Val Asp
690                 695                 700

Ser Asn Gly Asn Val Ile Val Ala Asp Trp Gly Asn Ser Arg Ile Gln
705                 710                 715                 720

Val Phe Asp Gly Ser Gly Ser Phe Leu Ser Tyr Ile Asn Thr Ser Ala
            725                 730                 735

Asp Pro Leu Tyr Gly Pro Gln Gly Leu Ala Leu Thr Ser Asp Gly His
        740                 745                 750

Val Val Val Ala Asp Ser Gly Asn His Cys Phe Lys Val Tyr Arg Tyr
    755                 760                 765

Leu Gln
770

<210> SEQ ID NO 9
<211> LENGTH: 761
<212> TYPE: PRT
<213> ORGANISM: Rattus norvegicus
```

<300> PUBLICATION INFORMATION:
<308> DATABASE ACCESSION NUMBER: NCBI NP_001102022
<309> DATABASE ENTRY DATE: 2009-05-11
<313> RELEVANT RESIDUES IN SEQ ID NO: (1)..(761)

<400> SEQUENCE: 9

```
Met Gln Arg Ala Gly Ser Arg Thr Ala Gly Pro Thr Cys Gln Trp Ser
1               5                   10                  15

Arg Met Ala Ser Glu Gly Ala Ser Ile Pro Ser Pro Val Val Arg Gln
            20                  25                  30

Ile Asp Lys Gln Phe Leu Ile Cys Ser Ile Cys Leu Glu Arg Tyr Lys
        35                  40                  45

Asn Pro Lys Val Leu Pro Cys Leu His Thr Phe Cys Glu Arg Cys Leu
    50                  55                  60

Gln Asn Tyr Ile Pro Ala His Ser Leu Thr Leu Ser Cys Pro Val Cys
65                  70                  75                  80

Arg Gln Thr Ser Ile Leu Pro Glu Lys Gly Val Ala Ala Leu Gln Asn
                85                  90                  95

Asn Phe Phe Ile Thr Asn Leu Met Asp Val Leu Gln Arg Thr Pro Gly
            100                 105                 110

Ser Asn Gly Glu Asp Pro Ser Ile Leu Gln Thr Val Thr Ala Val Ala
        115                 120                 125

Ala Gly Lys Pro Leu Ser Cys Pro Asn His Asp Gly Asn Val Met Glu
    130                 135                 140

Phe Tyr Cys Gln Ser Cys Glu Thr Ala Met Cys Arg Glu Cys Thr Glu
145                 150                 155                 160

Gly Glu His Ala Glu His Pro Thr Val Pro Leu Lys Asp Val Val Glu
                165                 170                 175

Gln His Lys Ala Ser Leu Gln Val Gln Leu Asp Ala Val Asn Lys Arg
            180                 185                 190

Leu Pro Glu Ile Asp Ser Ala Leu Gln Phe Ile Ser Glu Ile His
        195                 200                 205

Gln Leu Thr Asn Gln Lys Ala Ser Ile Val Asp Asp Ile His Ser Thr
    210                 215                 220

Phe Asp Glu Leu Gln Lys Thr Leu Asn Val Arg Lys Ser Val Leu Leu
225                 230                 235                 240

Met Glu Leu Glu Val Asn Tyr Gly Leu Lys His Lys Val Leu Gln Ser
                245                 250                 255

Gln Leu Asp Thr Leu Leu Gln Gly Gln Glu Ser Ile Lys Ser Cys Ser
            260                 265                 270

Asn Phe Thr Ala Gln Ala Leu Asn His Gly Thr Glu Thr Glu Val Leu
        275                 280                 285

Leu Val Lys Lys Gln Met Ser Glu Lys Leu Asn Glu Leu Ala Asp Gln
    290                 295                 300

Asp Phe Pro Leu His Pro Arg Glu Asn Asp Gln Leu Asp Phe Ile Val
305                 310                 315                 320

Glu Thr Glu Gly Leu Lys Lys Ser Ile His Asn Leu Gly Thr Ile Leu
                325                 330                 335

Thr Thr Asn Ala Val Ala Ser Glu Thr Val Ala Thr Gly Glu Gly Leu
            340                 345                 350

Arg Gln Thr Ile Ile Gly Gln Pro Met Ser Val Thr Ile Thr Thr Lys
        355                 360                 365

Asp Lys Asp Gly Glu Leu Cys Lys Thr Gly Asn Ala Tyr Leu Thr Ala
    370                 375                 380

Glu Leu Ser Thr Pro Asp Gly Ser Val Ala Asp Gly Glu Ile Leu Asp
```

```
            385                 390                 395                 400
Asn Lys Asn Gly Thr Tyr Glu Phe Leu Tyr Thr Val Gln Lys Glu Gly
                    405                 410                 415

Asp Phe Thr Leu Ser Leu Arg Leu Tyr Asp Gln His Ile Arg Gly Ser
                420                 425                 430

Pro Phe Lys Leu Lys Val Ile Arg Ser Ala Asp Val Ser Pro Thr Thr
            435                 440                 445

Glu Gly Val Lys Arg Val Lys Ser Pro Gly Ser Gly His Val Lys
        450                 455                 460

Gln Lys Ala Val Lys Arg Pro Ala Ser Met Tyr Ser Thr Gly Lys Arg
465                 470                 475                 480

Lys Glu Asn Pro Ile Glu Asp Leu Ile Phe Arg Val Gly Thr Lys
                485                 490                 495

Gly Arg Asn Lys Gly Glu Phe Thr Asn Leu Gln Gly Val Ala Ala Ser
                500                 505                 510

Thr Ser Gly Lys Ile Leu Ile Ala Asp Ser Asn Asn Gln Cys Val Gln
            515                 520                 525

Ile Phe Ser Asn Asp Gly Gln Phe Lys Ser Arg Phe Gly Ile Arg Gly
        530                 535                 540

Arg Ser Pro Gly Gln Leu Gln Arg Pro Thr Gly Val Ala Val His Pro
545                 550                 555                 560

Ser Gly Asp Ile Ile Ala Asp Tyr Asp Asn Lys Trp Val Ser Ile
                565                 570                 575

Phe Ser Asn Asp Gly Lys Phe Lys Thr Lys Ile Gly Ser Gly Lys Leu
                580                 585                 590

Met Gly Pro Lys Gly Val Ser Val Asp Arg Asn Gly His Ile Ile Val
            595                 600                 605

Val Asp Asn Lys Ala Cys Cys Val Phe Ile Phe Gln Pro Asn Gly Lys
        610                 615                 620

Ile Val Thr Arg Phe Gly Ser Arg Gly Asn Gly Asp Arg Gln Phe Ala
625                 630                 635                 640

Gly Pro His Phe Ala Ala Val Asn Ser Ser Asn Glu Ile Ile Thr
                645                 650                 655

Asp Phe His Asn His Ser Val Lys Val Phe Asn Gln Glu Gly Glu Phe
            660                 665                 670

Met Leu Lys Phe Gly Ser Asn Gly Glu Gly Asn Gly Gln Phe Asn Ala
        675                 680                 685

Pro Thr Gly Val Ala Val Asp Ser Asn Gly Asn Ile Ile Val Ala Asp
        690                 695                 700

Trp Gly Asn Ser Arg Ile Gln Val Phe Asp Gly Ser Gly Ser Phe Leu
705                 710                 715                 720

Ser Tyr Ile Asn Thr Ser Ala Asp Pro Leu Tyr Gly Pro Gln Gly Leu
                725                 730                 735

Ala Leu Thr Ser Asp Gly His Val Val Ala Asp Ser Gly Asn His
                740                 745                 750

Cys Phe Lys Val Tyr Arg Tyr Leu Gln
            755                 760

<210> SEQ ID NO 10
<211> LENGTH: 760
<212> TYPE: PRT
<213> ORGANISM: Xenopus tropicalis
<300> PUBLICATION INFORMATION:
<308> DATABASE ACCESSION NUMBER: GenBank AAH75100
<309> DATABASE ENTRY DATE: 2006-07-15
<313> RELEVANT RESIDUES IN SEQ ID NO: (1)..(760)
```

<400> SEQUENCE: 10

```
Met Ala Ser Glu Gly Ser Asn Ile Pro Ser Pro Val Val Arg Gln Ile
 1               5                  10                  15

Asp Lys Gln Phe Leu Ile Cys Ser Ile Cys Leu Asp Arg Tyr Lys Asn
             20                  25                  30

Pro Lys Val Leu Pro Cys Leu His Thr Phe Cys Glu Arg Cys Leu Gln
         35                  40                  45

Asn Tyr Ile Pro Ala His Ser Leu Thr Leu Ser Cys Pro Val Cys Arg
     50                  55                  60

Gln Thr Ser Ile Leu Pro Glu Lys Gly Val Ser Ala Leu Gln Asn Asn
 65                  70                  75                  80

Phe Phe Ile Thr Asn Leu Met Asp Val Leu Gln Arg Ser Pro Asp Asn
                 85                  90                  95

Gly Ile Glu Glu Ser Ser Ile Leu Glu Thr Val Ser Ala Val Ala Ala
            100                 105                 110

Gly Lys Pro Leu Ser Cys Pro Asn His Asp Gly Asn Val Met Glu Phe
            115                 120                 125

Tyr Cys Gln Ser Cys Glu Thr Ala Met Cys Gln Asp Cys Thr Gly Gly
    130                 135                 140

Glu His Ala Glu His Pro Thr Val Pro Leu Lys Asp Val Val Glu Gln
145                 150                 155                 160

His Lys Ala Ala Leu Gln Ala Gln Leu Asp Ala Val Lys Lys Arg Leu
                165                 170                 175

Pro Glu Ile Asp Ser Ala Leu Gln Cys Val Ser Glu Ile Val Asn Gln
            180                 185                 190

Leu Ala Ser Gln Lys Thr Ser Ile Val Glu Glu Ile His Ser Thr Phe
        195                 200                 205

Asp Asp Leu Gln Lys Thr Leu Asn Val Arg Lys Ser Val Leu Leu Met
    210                 215                 220

Glu Leu Glu Val Asn Tyr Gly Leu Lys His Lys Val Leu Gln Ala Gln
225                 230                 235                 240

Leu Asp Thr Leu Ile Glu Gly Gln Glu Ser Ile Lys Ser Cys Thr Thr
                245                 250                 255

Phe Thr Ala Gln Ala Leu Asn His Gly Thr Glu Thr Glu Val Leu Leu
            260                 265                 270

Val Lys Lys Gln Met Ser Asp Lys Leu Asn Glu Leu Ala Glu Gln Asp
        275                 280                 285

Phe Pro Leu Gln Pro His Glu Asn Asp Gln Leu Asp Phe Ile Val Glu
    290                 295                 300

Thr Glu Gly Leu Lys Lys Ser Ile His Asn Leu Gly Thr Ile Leu Thr
305                 310                 315                 320

Thr Asn Ala Val Ala Ser Glu Thr Val Ala Thr Gly Glu Gly Leu Arg
                325                 330                 335

Gln Ser Val Ile Gly Gln Pro Met Ser Val Thr Ile Thr Thr Lys Asp
            340                 345                 350

Lys Asp Gly Glu Leu Cys Lys Thr Gly Ser Ala Tyr Ile Ser Ala Glu
        355                 360                 365

Leu Phe Thr Pro Asp Gly Ser Val Thr Asp Gly Glu Val Val Asp Asn
    370                 375                 380

Lys Asn Gly Thr Tyr Glu Phe Ser Tyr Thr Ile Pro Thr Glu Gly Asp
385                 390                 395                 400

Phe Thr Leu Ser Leu Arg Leu Tyr Asp Gln His Ile Lys Gly Ser Pro
                405                 410                 415
```

```
Phe Lys Leu Lys Val Val Lys Ser Ala Asp Val Ser Pro Thr Thr Glu
        420                 425                 430
Gly Val Lys Arg Arg Val Lys Ser Pro Gly Ser Gly His Val Lys Gln
            435                 440                 445
Lys Ala Val Lys Arg Pro Ala Ser Met Tyr Ser Thr Gly Lys Arg Lys
        450                 455                 460
Glu Asn Pro Ile Glu Asp Leu Ile Phe Arg Val Gly Ser Arg Lys
465                 470                 475                 480
Asp Glu Asp Val Arg Ser Leu Thr Gly Thr Lys Gly Arg Asn Lys Gly
                485                 490                 495
Glu Phe Thr Asn Leu Gln Gly Val Ala Ala Ser Thr Asn Gly Lys Ile
            500                 505                 510
Leu Ile Ala Asp Ser Asn Asn Gln Cys Val Gln Ile Phe Ser Asn Asp
            515                 520                 525
Gly Gln Phe Lys Ser Arg Phe Gly Ile Arg Gly Arg Ser Pro Gly Gln
            530                 535                 540
Leu Gln Arg Pro Thr Gly Val Ala Val His Pro Ser Gly Asp Ile Ile
545                 550                 555                 560
Ile Ala Asp Tyr Asp Asn Lys Trp Val Ser Ile Phe Ser Ala Asp Gly
                565                 570                 575
Lys Phe Lys Thr Lys Ile Gly Ser Gly Lys Leu Met Gly Pro Lys Gly
            580                 585                 590
Val Ser Val Asp Arg Asn Gly His Ile Ile Val Val Asp Asn Lys Ala
            595                 600                 605
Cys Cys Val Phe Ile Phe Gln Pro Asn Gly Lys Ile Val Thr Arg Phe
        610                 615                 620
Gly Ser Arg Gly Asn Gly Asp Lys Gln Phe Ala Gly Thr Leu Asp Gly
625                 630                 635                 640
Pro His Phe Ala Ala Val Asn Ser Asn Asn Glu Ile Ile Val Thr Asp
                645                 650                 655
Phe His Asn His Ser Val Lys Val Phe Asn Gln Asp Gly Glu Phe Ile
            660                 665                 670
Leu Lys Phe Gly Ser Asn Gly Glu Gly Asn Gly Gln Phe Asn Ala Pro
        675                 680                 685
Thr Gly Val Ala Val Asp Ser Asn Gly Asn Ile Ile Val Ala Asp Trp
        690                 695                 700
Gly Asn Ser Arg Ile Gln Val Phe Asp Gly Ser Gly Ser Phe Leu Ser
705                 710                 715                 720
Tyr Ile Asn Thr Ser Ala Asp Pro Leu Tyr Gly Pro Gln Gly Leu Ser
                725                 730                 735
Leu Thr Ser Asp Gly His Val Val Ala Asp Ser Gly Asn His Cys
            740                 745                 750
Phe Lys Val Tyr Arg Tyr Leu Gln
        755                 760

<210> SEQ ID NO 11
<211> LENGTH: 744
<212> TYPE: PRT
<213> ORGANISM: Xenopus laevis
<300> PUBLICATION INFORMATION:
<308> DATABASE ACCESSION NUMBER: GenBank AAH74184
<309> DATABASE ENTRY DATE: 2004-08-03
<313> RELEVANT RESIDUES IN SEQ ID NO: (1)..(744)

<400> SEQUENCE: 11

Met Ala Ser Glu Gly Ser Asn Ile Pro Ser Pro Val Val Arg Gln Ile
```

```
          1               5                  10                 15
Asp Lys Gln Phe Leu Ile Cys Ser Ile Cys Leu Asp Arg Tyr Lys Asn
                 20                 25                 30

Pro Lys Val Leu Pro Cys Leu His Thr Phe Cys Glu Arg Cys Leu Gln
                 35                 40                 45

Asn Tyr Ile Pro Ala His Ser Leu Thr Leu Ser Cys Pro Val Cys Arg
 50                 55                 60

Gln Thr Ser Ile Leu Pro Glu Lys Gly Val Ser Ala Leu Gln Asn Asn
 65                 70                 75                 80

Phe Phe Ile Thr Asn Leu Met Asp Val Leu Gln Arg Ser Pro Asp Asn
                 85                 90                 95

Gly Ile Glu Glu Ser Ser Ile Leu Glu Thr Val Ser Ala Val Ala Ala
                100                105                110

Gly Lys Pro Leu Ser Cys Pro Asn His Asp Gly Asn Val Met Glu Phe
                115                120                125

Tyr Cys Gln Ser Cys Glu Thr Ala Met Cys Gln Asp Cys Thr Gly Gly
                130                135                140

Glu His Ala Glu His Pro Thr Val Pro Leu Lys Asp Val Val Glu Gln
145                150                155                160

His Lys Ala Ala Leu His Thr Gln Leu Asp Ala Val Lys Lys Arg Leu
                165                170                175

Pro Glu Ile Asp Ser Ala Leu Gln Cys Val Ser Glu Ile Val Asn Gln
                180                185                190

Leu Ala Ser Gln Lys Ser Asn Ile Val Glu Glu Ile His Ser Thr Phe
                195                200                205

Asp Asp Leu Gln Lys Thr Leu Asn Val Arg Lys Ser Val Leu Leu Met
210                215                220

Glu Leu Glu Val Asn Tyr Gly Val Lys His Lys Val Leu Gln Thr Gln
225                230                235                240

Leu Asp Thr Leu Ile Glu Gly Gln Glu Ser Ile Lys Ser Cys Thr Thr
                245                250                255

Phe Thr Ala Gln Ala Leu Asn His Gly Thr Glu Thr Glu Val Leu Leu
                260                265                270

Val Lys Lys Gln Met Ser Asp Lys Leu Asn Glu Leu Ala Glu Gln Asp
                275                280                285

Phe Pro Leu Gln Pro His Glu Asn Asp Gln Leu Asp Phe Ile Val Glu
                290                295                300

Thr Glu Gly Leu Lys Lys Ser Ile His Asn Leu Gly Thr Ile Leu Thr
305                310                315                320

Thr Asn Ala Val Ala Ser Glu Thr Val Ala Thr Gly Glu Gly Leu Arg
                325                330                335

Gln Ser Val Ile Gly Gln Pro Met Ser Val Thr Ile Thr Thr Lys Asp
                340                345                350

Lys Asp Gly Glu Leu Cys Lys Thr Gly Ser Ala Tyr Ile Ser Ala Glu
                355                360                365

Leu Leu Arg Pro Asp Gly Ser Gly Thr Asp Gly Glu Ile Val Asp Asn
                370                375                380

Lys Asn Gly Thr Tyr Glu Phe Ser Tyr Thr Ile Pro Thr Glu Gly Asp
385                390                395                400

Phe Thr Leu Ser Leu Arg Leu Tyr Asp Gln His Ile Lys Gly Ser Pro
                405                410                415

Phe Lys Leu Lys Val Ala Lys Ser Ala Asp Val Ser Pro Thr Ser Glu
                420                425                430
```

```
Gly Val Lys Arg Arg Val Lys Ser Pro Gly Gly His Val Lys Gln
        435                 440                 445

Lys Ala Val Lys Arg Pro Ala Ser Met Tyr Ser Thr Gly Lys Arg Lys
        450                 455                 460

Glu Asn Pro Ile Glu Asp Asp Leu Ile Phe Arg Val Gly Thr Lys Gly
465                 470                 475                 480

Arg Asn Lys Gly Glu Phe Thr Asn Leu Gln Gly Val Ala Ala Ser Thr
                485                 490                 495

Asn Gly Lys Ile Leu Ile Ala Asp Ser Asn Asn Gln Cys Val Gln Ile
                    500                 505                 510

Phe Ser Asn Asp Gly Gln Phe Lys Ser Arg Phe Gly Ile Arg Gly Arg
        515                 520                 525

Ser Pro Gly Gln Leu Gln Arg Pro Thr Gly Val Ala Val His Pro Ser
        530                 535                 540

Gly Asp Ile Ile Ile Ala Asp Tyr Asp Asn Lys Trp Val Ser Ile Phe
545                 550                 555                 560

Ser Ala Asp Gly Lys Phe Lys Thr Lys Ile Gly Ser Gly Lys Leu Met
                565                 570                 575

Gly Pro Lys Gly Val Ser Val Asp Arg Asn Gly His Ile Ile Val Val
                    580                 585                 590

Asp Asn Lys Ala Cys Cys Val Phe Ile Phe Gln Pro Asn Gly Lys Ile
        595                 600                 605

Val Thr Arg Phe Gly Ser Arg Gly Asn Gly Asp Lys Gln Phe Ala Gly
        610                 615                 620

Pro His Phe Ala Ala Val Asn Ser Asn Asn Glu Ile Ile Val Thr Asp
625                 630                 635                 640

Phe His Asn His Ser Val Lys Val Phe Asn Gln Asp Gly Glu Phe Ile
                645                 650                 655

Leu Lys Phe Gly Ser Asn Gly Glu Gly Asn Gly Gln Phe Asn Ala Pro
                    660                 665                 670

Thr Gly Val Ala Val Asp Ser Asn Gly Asn Ile Ile Val Ala Asp Trp
        675                 680                 685

Gly Asn Ser Arg Ile Gln Val Phe Asp Gly Ser Gly Ser Phe Leu Ser
        690                 695                 700

Tyr Ile Asn Thr Ser Ala Asp Pro Leu Tyr Gly Pro Gln Gly Leu Ser
705                 710                 715                 720

Leu Thr Ser Asp Gly His Val Val Ala Asp Ser Gly Asn His Cys
                725                 730                 735

Phe Lys Val Tyr Arg Tyr Leu Gln
            740
```

<210> SEQ ID NO 12
<211> LENGTH: 744
<212> TYPE: PRT
<213> ORGANISM: Danio rerio
<300> PUBLICATION INFORMATION:
<308> DATABASE ACCESSION NUMBER: NCBI NP_001014393
<309> DATABASE ENTRY DATE: 2007-10-30
<313> RELEVANT RESIDUES IN SEQ ID NO: (1)..(744)

<400> SEQUENCE: 12

```
Met Ala Thr Asp Ala Ser Thr Leu Pro Ser Pro Val Val Arg Gln Ile
1               5                   10                  15

Asp Lys Gln Phe Leu Ile Cys Ser Ile Cys Leu Asp Arg Tyr Asn Asn
                20                  25                  30

Pro Lys Val Leu Pro Cys Leu His Thr Phe Cys Glu Arg Cys Leu Gln
        35                  40                  45
```

```
Asn Tyr Ile Pro Pro His Ser Leu Thr Leu Ser Cys Pro Val Cys Arg
     50                  55                  60

Gln Thr Ser Ile Leu Pro Glu Lys Gly Val Ala Ala Leu Gln Ser Asn
 65                  70                  75                  80

Phe Phe Ile Thr Asn Leu Met Glu Val Leu Lys Lys Ser Pro Asn Ser
                 85                  90                  95

Asn Leu Ser Glu Asp Tyr Thr Asp Ala Ile Asn Gly Val Ala Thr Gly
            100                 105                 110

Gln Pro Leu Ser Cys Pro Asn His Gly Gly Asn Val Met Glu Phe Tyr
        115                 120                 125

Cys Pro Pro Cys Glu Thr Ala Met Cys Glu Glu Cys Thr Ser Gly Glu
    130                 135                 140

His Ala Glu His Ala Thr Val Pro Leu Lys Asp Val Leu Glu Gln His
145                 150                 155                 160

Lys Ala Ser Leu Gln Glu Gln Leu Asp Ala Val Lys Asn Arg Leu Pro
                165                 170                 175

Glu Ile Glu Ser Ala Leu Glu Val Leu Ser Glu Ile Leu Gln Gln Leu
            180                 185                 190

Ser Ser Gln Lys Ser Ser Ile Glu Glu Met Ile His Ala Thr Phe Glu
        195                 200                 205

Glu Leu Gln Lys Thr Leu Asn Val Arg Lys Ser Val Leu Leu Met Glu
    210                 215                 220

Leu Glu Val Asn Tyr Gly Leu Lys Gln Lys Val Leu Gln Thr Gln Leu
225                 230                 235                 240

Glu Ser Leu Leu Gln Gly Gln Asp Gly Ile Arg Ser Ser Cys Ser Phe
                245                 250                 255

Thr Glu Gln Ala Leu Asn His Gly Ser Glu Ala Glu Val Leu Leu Val
            260                 265                 270

Lys Lys Gln Met Ser Glu Arg Leu Asp Glu Leu Ala Asn Gln Glu Leu
        275                 280                 285

Pro Leu Arg Pro Glu Glu Asn Asn Gln Leu Asp Phe Leu Val Glu Thr
    290                 295                 300

Asp Gly Leu Arg Lys Ser Ile His Asn Leu Gly Ala Ile Val Thr Thr
305                 310                 315                 320

Asn Ala Val Ala Ala Glu Thr Val Ala Thr Gly Glu Gly Leu Arg His
                325                 330                 335

Cys Ile Val Gly Gln Leu Thr Ser Val Thr Val Thr Thr Lys Asp Arg
            340                 345                 350

Asp Gly Gly Leu Cys Arg Thr Gly Asn Ala Leu Leu Ile Ala Asp Leu
        355                 360                 365

Ser Ala Ile Asp Gly Ser Ile Val Gly Glu Gly Lys Val Thr Asp His
    370                 375                 380

Lys Asn Gly Thr Tyr Glu Phe Val Tyr Ser Val Pro Cys Glu Gly Arg
385                 390                 395                 400

Phe Thr Leu Thr Leu Lys Leu Tyr Asp Gln His Ile Arg Gly Ser Pro
                405                 410                 415

Phe Ser Ile Arg Ala Asn Lys Pro Thr Asp Ile Ser Leu Thr Ala Asp
            420                 425                 430

Val Asp Lys Lys Arg Leu Lys Ser Pro Gly Asn Ser His Val Lys Gln
        435                 440                 445

Arg Ala Ile Lys Arg Pro Ala Ser Met Tyr Ser Thr Gly Lys Arg Lys
    450                 455                 460

Glu Asn Pro Ile Glu Asp Asp Leu Ile Phe Arg Ile Gly Thr Lys Gly
```

```
                        465                 470                 475                 480
Arg Asn Lys Gly Glu Phe Thr Asn Leu Gln Gly Val Ala Ala Ser Ser
                485                 490                 495

Val Gly Lys Val Leu Ile Ala Asp Ser Asn Asn Gln Cys Val Gln Ile
                500                 505                 510

Phe Leu Asn Asp Gly Gln Phe Lys Gly Arg Phe Gly Ile Arg Gly Arg
            515                 520                 525

Ser Pro Gly Gln Leu Gln Arg Pro Thr Gly Val Ala Val His Pro Ser
        530                 535                 540

Gly Asp Ile Ile Ile Ala Asp Tyr Asp Asn Lys Trp Val Ser Ile Phe
545                 550                 555                 560

Ser Ser Asp Gly Lys Phe Lys Ser Lys Ile Gly Ser Gly Lys Leu Met
                565                 570                 575

Gly Pro Lys Gly Val Ser Val Asp Arg Asn Gly His Ile Ile Val Val
                580                 585                 590

Asp Asn Lys Ser Cys Cys Val Phe Ile Phe Gln Pro Asn Gly Lys Leu
            595                 600                 605

Val Ser Lys Phe Gly Asn Arg Gly Asn Ser Asp Lys Gln Phe Ala Gly
        610                 615                 620

Pro His Phe Ala Ala Val Asn Gln Asn Asn Glu Val Ile Val Thr Asp
625                 630                 635                 640

Phe His Asn His Ser Val Lys Val Phe Ser Pro Glu Gly Glu Phe Ile
                645                 650                 655

Leu Lys Phe Gly Ser Asn Gly Glu Gly Asn Gly Gln Phe Asn Ala Pro
                660                 665                 670

Thr Gly Val Ala Val Asp Ala Asn Gly Asn Ile Ile Val Ala Asp Trp
                675                 680                 685

Gly Asn Ser Arg Ile Gln Val Phe Asp Ser Ser Gly Ser Phe Leu Ser
            690                 695                 700

Tyr Ile Asn Thr Ser Ala Asp Pro Leu Tyr Gly Pro Gln Gly Leu Ala
705                 710                 715                 720

Leu Thr Ser Asp Gly His Val Val Val Ala Asp Ser Gly Asn His Cys
                725                 730                 735

Phe Lys Val Tyr Arg Tyr Leu Gln
            740
```

INTERACTION OF BIM WITH TRIM2

CROSS-REFERENCES TO PRIORITY APPLICATIONS

This application is a continuation of U.S. patent application Ser. No. 12/178,491, filed Jul. 23, 2008, which in turn is based upon and claims the benefit under 35 U.S.C. §119(e) of U.S. Provisional Patent Application Ser. No. 60/961,848, filed Jul. 23, 2007. These applications are incorporated herein by reference in their entireties for all purposes.

GOVERNMENT LICENSE RIGHTS

This invention was made with U.S. Government support from National Institutes of Health R01 grants NS059588, NS024728, NS039016; and R21 grants NS050669 and NS054023. The U.S. Government thus may have certain license rights in the invention.

SEQUENCE LISTING

A sequence listing is being filed concurrently by electronic submission of a text file named "20100129_Sequence_Listing_LHY309BCIP_ST25.txt," which was created on Jan. 29, 2010, and has a size of 54.0 KB (55,349 bytes). The sequence listing of the text file is incorporated herein by reference.

BACKGROUND

Apoptosis is a form of cell death mediated by an intracellular program. The intracellular program proceeds through a series of biochemical events that result in various changes to cell morphology, including blebbing, cell shrinkage, nuclear fragmentation, chromatin condensation, and DNA fragmentation. Proteolytic enzymes termed caspases are thought to be primarily responsible for these hallmarks of apoptosis.

Apoptosis is fundamental to various biological processes, such as adult homeostasis (i.e., to keep the number of cells relatively constant), response to injury (i.e., to kill damaged cells), development (e.g., to help pattern developing tissues), and maturation of the immune system (e.g., to remove lymphocytes that are ineffective and/or harmful), among others. Accordingly, many diseases are associated with a change in the rate of apoptosis. For example, tumor cells may have a resistance to apoptosis that provides a selective growth advantage over normal cells. In contrast, unwanted apoptosis may cause the neurological damage prevalent in various neurological diseases, such as stroke, Parkinson's disease, and Alzheimer's disease. Members of the Bcl-2 family regulate activation of the caspases. This family consists of two groups, namely, pro-death proteins (e.g., Bax) and pro-survival proteins (e.g., Bcl-2). The ratio of pro-death to pro-survival proteins within a cell generally determines whether the cell undergoes apoptosis or survives.

Bim protein is a pro-death member of the Bcl-2 family. The Bim protein is expressed as at least three protein isoforms of different length (i.e., $Bim_{EL}$, $Bim_L$, and $Bim_S$) having distinct potencies for promoting cell death, with the $Bim_S$ protein isoform being most potent. The Bim protein plays a critical role in mediating cell death in various cell types. Therefore, drugs that modify levels of Bim protein would facilitate treating diseases characterized by abnormally low or abnormally high levels of apoptosis.

The steady-state level of a protein within a cell is generally determined by the rate at which the protein is synthesized relative to the rate at which the protein is degraded (catabolized). The primary mechanism for protein catabolism in cells is the Ubiquitin Proteasome Pathway (UPP). Protein catabolism by the UPP involves two successive steps: (1) covalent attachment of multiple ubiquitin polypeptides to a protein substrate ("ubiquitination") to produce a ubiquitin-tagged protein; and (2) degradation of the ubiquitin-tagged protein by the 26S proteasome.

FIG. 1 shows a schematic flowchart 50 representing selected aspects of the UPP, including a ubiquitination portion 52 and a degradation portion 54. In the ubiquitination portion, an E3 ubiquitin ligase 56 (also termed an "E3 ligase") promotes conjugation of a ubiquitin polypeptide 58 to a protein substrate 60. In particular, the ubiquitin polypeptide is transferred to the protein substrate from an E2 ubiquitin-conjugating enzyme 62 (also termed an "E2 enzyme"), which serves as a ubiquitin donor. Before this transfer, in an earlier step not shown here, the E2 enzyme receives ubiquitin polypeptide 58 in an activated form from an E1 ubiquitin-activating enzyme. Then, E3 ligase 56 targets transfer, indicated by an arrow at 64, of ubiquitin polypeptide 58 from E2 enzyme 62 to protein substrate 60. To target this transfer of ubiquitin, the E3 ligase may interact with both the E2 enzyme and the protein substrate at the same time, as shown here, or may interact sequentially such that ubiquitin is received first by the E3 ligase from the E2 enzyme and then is transferred to the protein substrate. In any event, the transfer of a ubiquitin polypeptide to the protein substrate may be performed repeatedly, indicated at 66, to form a ubiquitin-tagged product 68 in which protein substrate 60 is conjugated to a plurality of ubiquitin polypeptides 58. In degradation portion 54 of FIG. 1, ubiquitin-tagged product 68 may be recognized and processed by the 26S proteasome to produce degradation products 70 and released ubiquitin polypeptides 58.

A cell may contain only a few types of E1 enzymes, a larger number of E2 enzymes, and an even greater diversity of E3 ligases. Consistent with this high diversity of E3 ligases employed by the cell, each E3 ligase is thought to play a primary role in substrate identification for degradation in the UPP. However, for most proteins, a corresponding E3 ligase that targets degradation has not yet been identified.

Bim protein has been reported to be ubiquitinated, which suggests that Bim protein is degraded in the Ubiquitin Proteasome Pathway using a Bim-selective E3 ligase. Furthermore, phosphorylation of Bim protein on Ser65 in humans (Ser69 in rat) by p42/p44 MAP kinase (MAPK) has been shown to be an essential step for Bim ubiquitination and proteasomal degradation. As a result, mitogen stimulation of cells, which increases the level of active MAP kinase, may produce increased Bim ubiquitination and degradation, and thus less Bim protein and increased cell survival. However, a Bim-selective E3 ligase that is MAPK-dependent for interaction with Bim protein has not been identified in the prior art, although such an E3 ligase would provide a valuable tool for drug design, clinical diagnostics, and treatment of disease.

SUMMARY

The present disclosure provides methods, compositions, and cells for drug screening based on interaction between a Bim polypeptide and a TRIM2 polypeptide. Methods and compositions for treating cancer based on tested levels of Bim and TRIM2 proteins are also provided.

BRIEF DESCRIPTION OF THE DRAWINGS

FIG. 17 is a graph presenting exemplary data on Bim and TRIM2 protein expression ratios in established breast cancer cell lines, in accordance with aspects of present disclosure.

FIG. 18 is a pair of immunoblots presenting exemplary data on expression of TRIM2 and Bim proteins in breast tumor samples, in accordance with aspects of present disclosure.

BRIEF DESCRIPTION OF THE LISTED SEQUENCES

Figure 1:
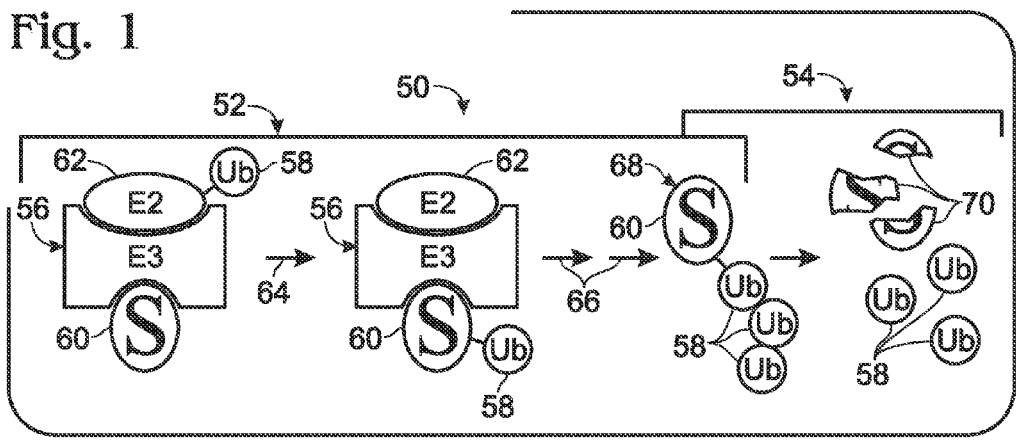
FIG. 1 is a schematic flowchart of selected aspects of the Ubiquitin Proteasome Pathway.

SEQ ID NOS:1-5 are amino acid sequences of respective human, mouse (*Mus musculus*), rat (*Rattus norvegicus*), horse (*Equus caballus*), and monkey (*Macaca mulatta*) $Bim_{EL}$ proteins.

SEQ ID NO:6 and SEQ ID NO:7 are amino acid sequences of distinct isoforms of a human TRIM2 protein.

SEQ ID NO:8 and SEQ ID NO:9 are amino acid sequences of respective mouse (*Mus musculus*) and rat (*Rattus norvegicus*) TRIM2 proteins.

SEQ ID NO:10 and SEQ ID NO:11 are amino acid sequences of frog TRIM2 proteins from *Xenopus tropicalis* and *Xenopus laevis*, respectively.

SEQ ID NO:12 is an amino acid sequence of a fish TRIM2 protein from Danio rerio.

DETAILED DESCRIPTION

The present disclosure provides methods, compositions, and cells for drug screening based on interaction between a Bim polypeptide and a TRIM2 polypeptide. Methods and compositions for treating cancer based on tested levels of Bim and TRIM2 proteins are also provided.

The method for drug screening may be used to develop new drugs for enhancing or inhibiting apoptosis. A plurality of assay mixtures may be formed. Each assay mixture may include a Bim polypeptide and a TRIM2 polypeptide (or an E2 polypeptide and a TRIM2 polypeptide) that interact with each other in the assay mixture (in the absence of a test compound). In some embodiments, one or both of the Bim and TRIM2 (or E2 and TRIM2) polypeptides may include a conjugated tag, such as an epitope tag, a luminescent tag, an enzyme tag, an affinity tag, or any combination thereof, among others. For example, the Bim and TRIM2 (or E2 and TRIM2) polypeptides may include distinct, conjugated luminescent tags, such as having respective Bim and TRIM2 (or E2 and TRIM2) portions conjugated to distinct fluorescent polypeptides. Each assay mixture also may include one or more test compounds, with different test compounds being present in at least some of the assay mixtures. Furthermore, each assay mixture also or alternatively may include a MAP kinase (MAPK) (since interaction between Bim and TRIM2 polypeptides may be increased by and/or dependent on MAPK activity), a cell extract, biological cells, or a combination thereof, among others. The biological cells may express one or both of the Bim and TRIM2 (or E2 and TRIM2) polypeptides, for example, both polypeptides may be expressed by the same cells or by respective distinct cells. Interaction of the Bim and TRIM2 (or E2 and TRIM2) polypeptides with each other in each assay mixture may be detected. Whether the test compounds affect the interaction of the Bim and TRIM2 (or E2 and TRIM2) polypeptides may be determined. At least one test compound then may be selected as a candidate drug for treatment of a disease characterized by an abnormal amount of cell death/apoptosis. The selection may be based at least in part on a determination that the at least one test compound affects interaction of the Bim and TRIM2 (or E2 and TRIM2) polypeptides.

The present disclosure also provides a composition for drug screening to develop new drugs for enhancing or inhibiting apoptosis. The composition may include engineered Bim and TRIM2 (or E2 and TRIM2) polypeptides that interact with one another. The composition further may include biological cells that express the engineered polypeptides.

The present disclosure further provides a method of treating cancer, such as breast cancer. One or more samples from a cancer patient may be tested for levels of TRIM2 protein (or RNA), Bim protein (or RNA), active MAPK protein (or MAPK RNA), or any combination thereof. The cancer patient may be treated with at least one drug (a Bim stabilizing agent) that inhibits degradation of Bim protein, if the tested levels of TRIM2 and Bim proteins or TRIM2, Bim, and active MAPK proteins meet one or more predefined conditions. Exemplary drugs that may be used to stabilize Bim include an inhibitor of proteasome activity or MAPK activity (e.g., via upstream inhibition of a MAPK kinase (MEK)), among others. In some embodiments, the cancer patient may be treated with a Bim stabilizing agent and a DNA targeting agent, such as doxorubicin, cisplatin, and/or cyclophosphamide, among others, if the tested levels of TRIM2 and Bim proteins meet one or more predefined conditions, such as based on whether a ratio of Bim and TRIM2 proteins meets a predefined condition.

Figure 2:
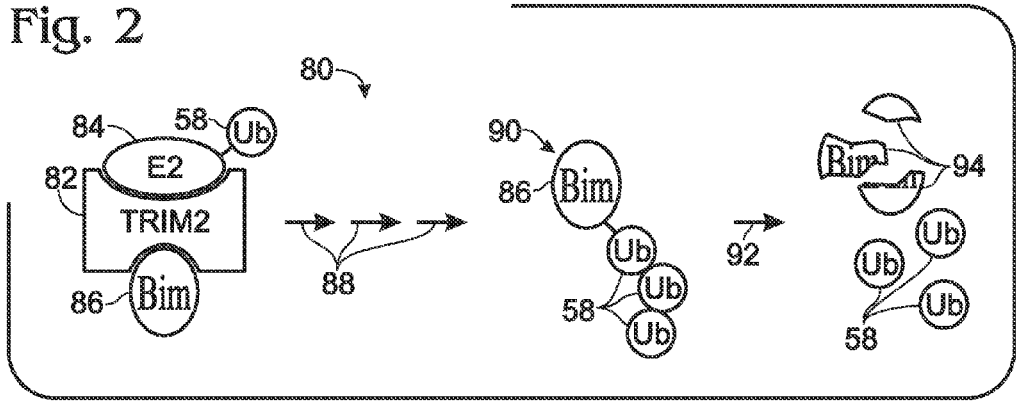
FIG. 2 is a schematic flowchart of an exemplary model of Bim protein degradation in the Ubiquitin Proteasome Pathway with TRIM2 protein functioning as an E3 ubiquitin ligase for the Bim protein, in accordance with aspects of the present disclosure.

FIG. 2 shows a schematic flowchart 80 of a model of Bim protein degradation in the Ubiquitin Proteasome Pathway. A TRIM2 protein 82 may function as a Bim-selective E3 ubiquitin ligase that promotes transfer of ubiquitin 58 from an E2 ubiquitin-conjugating enzyme 84 (an E2 enzyme) to a Bim protein 86. Accordingly, ubiquitin 58 may be transferred repeatedly, indicated by arrows at 88, from E2 enzyme 84 to Bim protein 86 to form a polyubiquitinated Bim protein 90. The polyubiquitinated Bim protein may be degraded by the 26S proteasome, indicated by the arrow at 92, to form Bim degradation products 94 and released ubiquitin polypeptides 58.

The mechanistic details presented in flowchart 80 are illustrative only and are not intended to provide a theory of operation that limits the scope of the claimed invention. For example, interaction of TRIM2 protein with Bim protein and/or E2 enzyme may involve other polypeptides not shown here and thus may or may not be via direct contact. Moreover, interaction of TRIM2 protein with Bim protein may be increased or may at least substantially require phosphorylation of the Bim protein, such as by MAPK. In addition, TRIM2 protein may not interact with E2 enzyme and Bim protein at the same time. Also, the interactions may or may not involve a dimer or higher order complex of E2 enzyme, TRIM2 protein, and/or Bim protein. Furthermore, Bim protein may be degraded as a monoubiquitinated form.

The present disclosure identifies the TRIM2 protein as an E3 ligase for Bim protein based on several lines of evidence (e.g., see Section VI). (1) TRIM2 protein was identified by its interaction with Bim protein in a complex mixture of proteins. (2) TRIM2 protein has a RING finger domain, which is a structural domain commonly found in E3 ubiquitin ligases. (3) The present disclosure presents data showing that Bim and TRIM2 polypeptides interact in several different assay systems, including a cell-free expression system and a cell lysate. (4) The present disclosure presents data showing that expression of Bim and TRIM2 proteins is inversely correlated in various cancer lines and tumor samples and also when TRIM2 protein expression is reduced by RNA interference. (5) The present disclosure presents data showing that interaction of Bim and TRIM2 polypeptides is inhibited by treatments that promote apoptosis, such as ischemia and upstream inhibition of MAPK activity in neuronal cultures. (6) The present disclosure presents data showing that a TRIM2 polypeptide interacts with several distinct E2 ubiquitin-conjugating enzymes.

The following sections describe further aspects of the present disclosure, including, among others, (I) interaction assays, (II) Bim, TRIM2, and E2 polypeptides, (III) test compounds, (IV) selecting a test compound as a candidate drug, (V) treating cancer based on testing for Bim and TRIM2 proteins, and (VI) examples.

I. Interaction Assays

Figure 3:
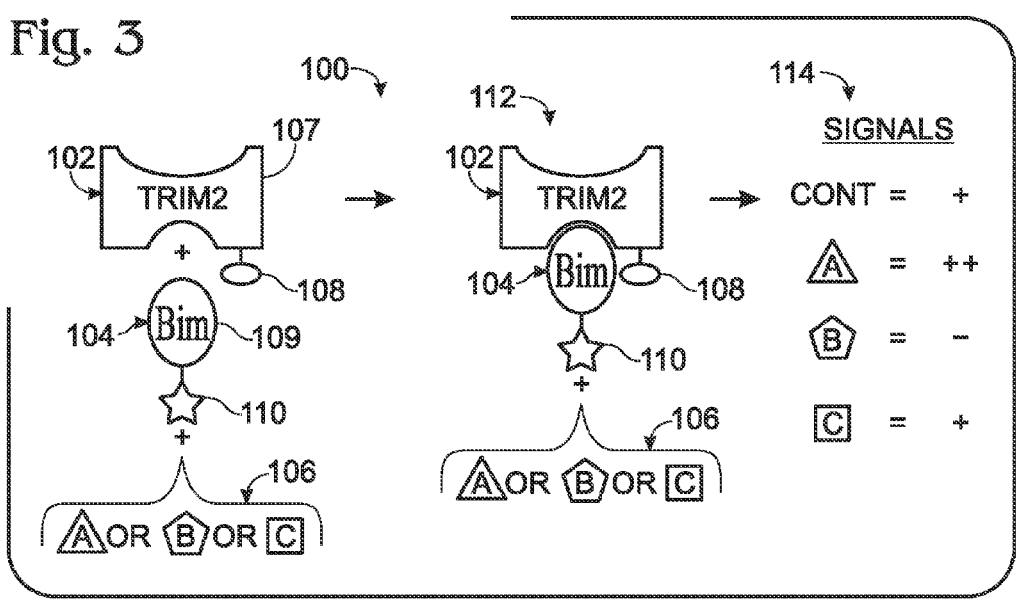
FIG. 3 is a schematic flowchart illustrating an exemplary method of drug screening based on interaction of a Bim polypeptide and a TRIM2 polypeptide, in accordance with aspects of the present disclosure.

FIG. 3 shows a schematic flowchart 100 illustrating an exemplary method of drug screening based on an interaction assay involving Bim and TRIM2 polypeptides. The assay may be performed using (1) a TRIM2 polypeptide 102, (2) a Bim polypeptide 104, and (3) one or more test compounds 106 (indicated here as A-C). One or both of TRIM2 polypeptide 102 and Bim polypeptide 104 may be tagged. For example, the TRIM2 polypeptide may include a TRIM2 portion 107 attached to a first tag 108. Alternatively, or in addition, the Bim polypeptide may include a Bim portion 109 attached to a second tag 110. Each tag may (or may not) be a polypeptide and may have any suitable size relative to its respective Bim or TRIM2 portion, such as being smaller or larger than the respective Bim or TRIM2 portion.

At least one assay mixture 112 including TRIM2 and Bim polypeptides 102, 104 and test compounds 106 may be formed. For example, each test compound (A-C) may be disposed in a respective, separate assay mixture with the Bim and TRIM2 polypeptides or two or more test compounds may be disposed in the same assay mixture with the Bim and TRIM2 polypeptides. In some embodiments, a plurality of assay mixtures may be formed and the assay mixtures may be disposed in respective wells of a microplate (e.g., a microtiter dish). Exemplary microplates may include 96, 384, or 1536 wells, among others. Furthermore, no test compound may be disposed in at least one assay mixture to provide a control.

The assay mixture may be formed by combining any suitable materials in any suitable order. The assay mixture may include cells that express one or both of the Bim and TRIM2 polypeptides, a cell extract containing one or both of the Bim and TRIM2 polypeptides, a kinase (e.g., a MAPK), a MAPK kinase (e.g., MEK1 and/or MEK2) inhibitor (e.g., U0126, PD98059, SL 327, etc.), or any combination thereof. The compound U0126 is 1,4-diamino-2,3-dicyano-1,4-bis(2-aminophenylthio)butadiene and has the following chemical structure:

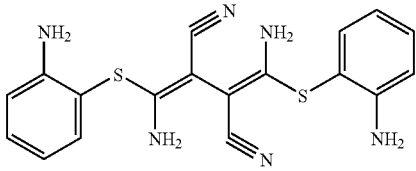

The compound PD98059 is 2-(2-Amino-3-methoxyphenyl)-4H-1-benzopyran-4-one and has the following chemical structure:

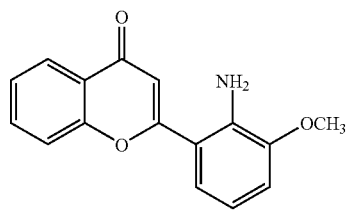

At least one component of the assay mixture (e.g., TRIM2 polypeptide 102 or Bim polypeptide 104) may be connected to a solid support (e.g., a membrane, a vessel wall, a bead, or the like).

Interaction of Bim and TRIM2 polypeptides 102, 104 in the assay mixtures may be detected as signals 114. For example, here, detected signals are listed for a control ("CONT"; no test compound) and test compounds A-C individually. The signals may be detected directly from the assay mixtures in a homogeneous assay, without separating bound and free polypeptides, such as in a homogeneous optical assay, or may be detected after performing at least one separation procedure on each assay mixture in a heterogeneous assay. The detected signals may be analyzed to determine whether the test compounds affect the interaction of Bim and TRIM2 polypeptides 102, 104. Analysis of the detected signals may include comparing a signal to a threshold value and/or to a control value, among others. For example, here, comparison of the detected signals shows that test compounds A, B, and C respectively increase, decrease, and have no effect on the interaction of Bim and TRIM2 polypeptides. In some examples, at least one test compound may be selected as a drug candidate for regulating apoptosis (i.e., increasing or decreasing apoptosis) based at least in part on a determination that the test compound affects the Bim-TRIM2 interaction. A "drug candidate" is a compound or composition that shows promise but requires further testing (e.g., in animals and/or clinical trials) before the drug candidate is approved for use as a drug in treating a particular condition.

Figure 4:
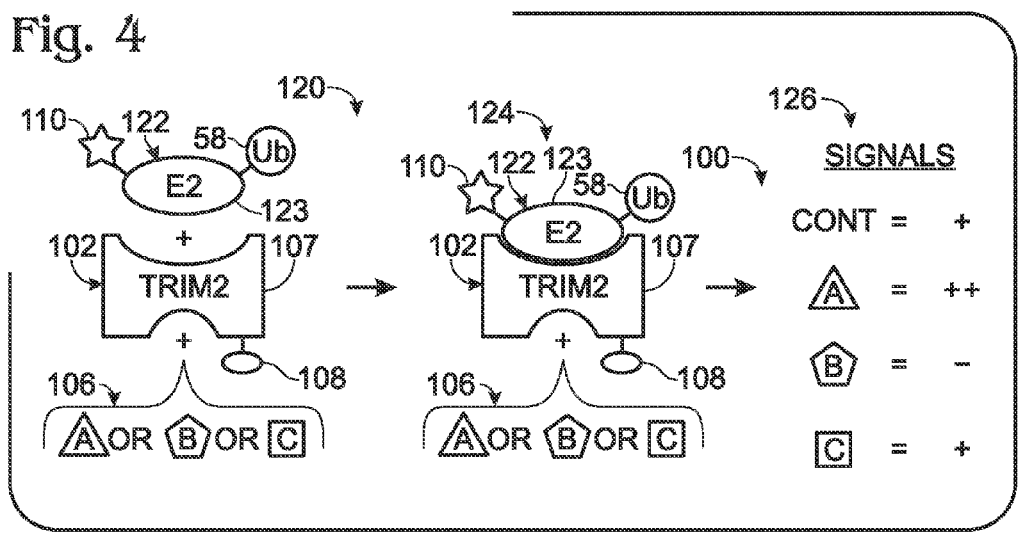
FIG. 4 is a schematic flowchart illustrating an exemplary method of drug screening based on interaction of a TRIM2 polypeptide and an E2 ubiquitin-conjugating enzyme polypeptide (i.e., an E2 polypeptide), in accordance with aspects of the present disclosure.

FIG. 4 shows a schematic flowchart 120 illustrating an exemplary method of drug screening based on an assay for interaction of a TRIM2 polypeptide and an E2 ubiquitin-conjugating enzyme polypeptide ("E2 polypeptide"). The assay may be performed using (1) TRIM2 polypeptide 102, (2) an E2 polypeptide 122 that corresponds or is identical to a particular E2 enzyme, and (3) one or more test compounds 106. One or both of TRIM2 polypeptide 102 and E2 polypeptide 122 may be tagged, such as including respective first and second tags 108, 110. Accordingly, the E2 polypeptide may include an E2 portion 123 attached to tag 110, and further may be conjugated to ubiquitin polypeptide 58.

At least one assay mixture 124 including TRIM2 and E2 polypeptides 102, 122 and one or more of test compounds 106 may be formed, and signals may be detected, indicated at 126. The assay mixture may include any of the components described above for Bim-TRIM interaction assays, and optionally may include a polypeptide corresponding or identical to Bim protein, an E1 ubiquitin-activating enzyme, ubiquitin, ATP, a MAPK (particularly an active MAPK, such as active ERK1/2), or any combination thereof. At least one component of the assay mixture (e.g., TRIM2 polypeptide 102, E2 polypeptide 122, or a Bim polypeptide, among others) may be connected to a solid support.

Figure 5:
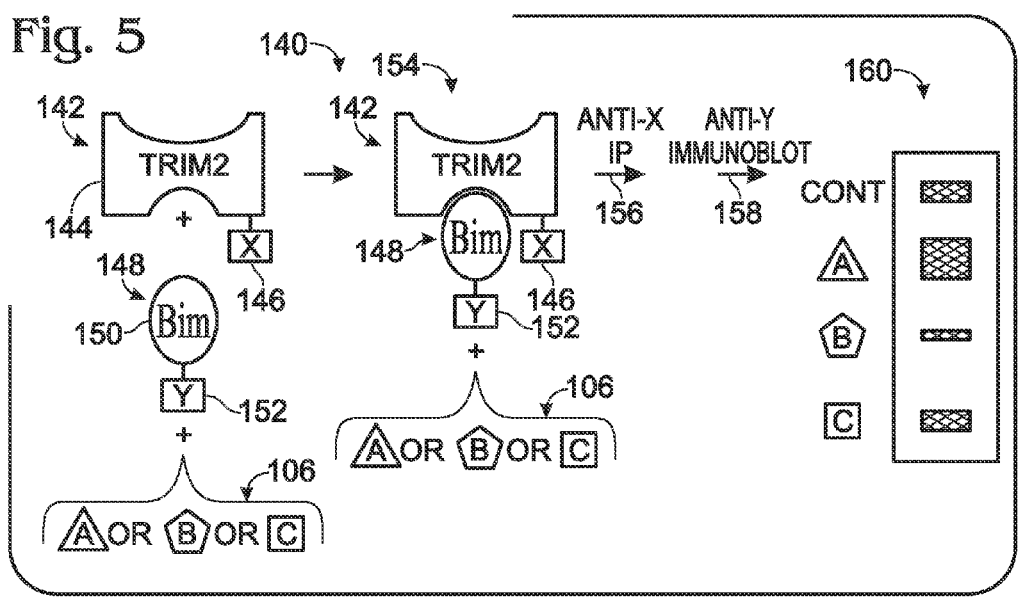
FIG. 5 is a schematic representation of an exemplary method of drug screening based on the use of one or more antibodies to facilitate detecting interaction of Bim and TRIM2 polypeptides, in accordance with aspects of the present disclosure.

FIG. 5 shows a schematic flowchart 140 illustrating an exemplary method of drug screening based on the use of one or more antibodies to facilitate detecting interaction of Bim and TRIM2 polypeptides. The assay may be performed using a TRIM2 polypeptide 142 that includes a TRIM2 portion 144 conjugated to a first epitope tag 146 ("X"), a Bim polypeptide 148 that includes a Bim portion 150 conjugated to a second epitope tag 152 ("Y"), and one or more test compounds 106 (e.g., A-C). In some embodiments, one or both of the epitope tags may be omitted. An exemplary first (or second) epitope tag 146 that may be suitable is a c-myc tag recognized by a monoclonal antibody (9E10) produced by immunizing mice with a synthetic peptide containing a c-myc epitope. An exemplary second (or first) epitope tag 152 that may be suitable is an HA tag that is recognized by a monoclonal antibody (6E2) produced by immunizing mice with a synthetic peptide containing an influenza hemagglutinin epitope.

The method may include any combination of the following exemplary procedures. At least one assay mixture 154 may be formed that includes TRIM2 polypeptide 142, Bim polypeptide 148, and one or more test compounds 106. The assay mixture may use any suitable buffer, salt, detergent, chelator, etc. An exemplary Tris buffer cocktail that may have a suitable composition for interaction assays includes 150 mM NaCl, 50 mM Tris-HCl (pH 8.0), 1.0% NP-40, 1 mM EDTA, and optionally may include protease inhibitors (aprotinin 1 µg/mL, leupeptin 2 µg/mL, pepstatin 1 µg/mL, and PMSF (10 µg/mL). The Tris buffer cocktail may be used to make a cell extract.

The assay mixture may be contacted with a first antibody, indicated at 156, that specifically binds to only one of polypeptides 142, 148. For example, the assay mixture may be contacted with an antibody against first epitope tag 146 or second epitope tag 152. Here, the first antibody is an anti-X antibody that recognizes the first epitope tag. Alternatively, the assay mixture may be contacted with an anti-TRIM2 antibody or an anti-Bim antibody that recognizes TRIM2 protein or Bim protein, respectively. In some embodiments, contacting the assay mixture with an antibody may bind one of polypeptides 142, 148 ("a first polypeptide") to a solid support, such as a bead, a membrane, or a vessel wall, among others. In some embodiments, after contacting the assay mixture with the first antibody, the first antibody and its bound first polypeptide may be separated from the assay mixture, such as by performing immunoprecipitation and/or one or more washing steps.

Material separated with the first antibody then may be analyzed for the presence of the other polypeptide ("the second polypeptide"), resulting from co-immunoprecipitation with (and thus interaction with) the first polypeptide, by any suitable mechanism, such as by contact with a second antibody that specifically binds the second polypeptide. For example, the separated material may be resolved by gel electrophoresis followed by immunoblotting with the second antibody, indicated at 158, to provide signals 160 indicative of the amount of interaction between TRIM2 and Bim polypeptides in the presence of each test compound (A-C)

relative to control (CONT). Here, the second antibody is an anti-Y antibody that recognizes the second epitope tag. In other embodiments, an antibody recognizing the TRIM2 polypeptide may be used for immunoprecipitation and an antibody recognizing the Bim polypeptide may be used for immunoblotting. In other embodiments, one or both of the Bim and TRIM2 polypeptides may be recognized using an antibody directed against Bim or TRIM2 protein.

Figure 6:
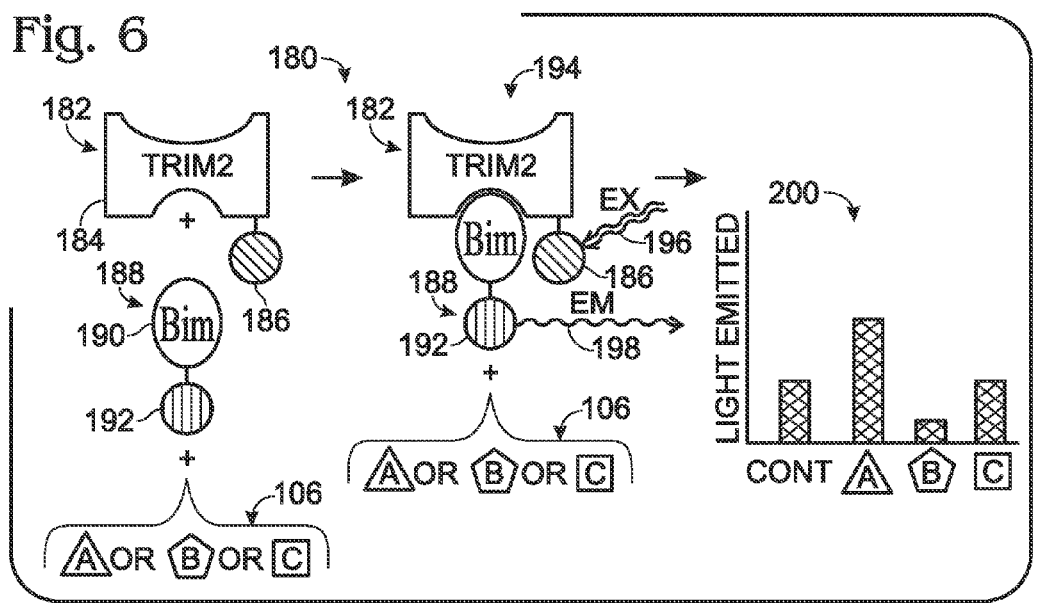
FIG. 6 is a schematic representation of an exemplary method of drug screening based on interaction of a Bim polypeptide and a TRIM2 polypeptide each including a distinct luminescent tag, in accordance with aspects of present disclosure.

FIG. 6 shows a schematic flowchart 180 illustrating an exemplary method of drug screening based on the use of Bim and TRIM2 polypeptides each having a distinct luminescent tag. The method may be performed using a TRIM2 polypeptide 182 that includes a TRIM2 portion 184 conjugated to a first luminescent tag 186, a Bim polypeptide 188 that includes a Bim portion 190 conjugated to a second luminescent tag 192, and one or more test compounds 106 (e.g., A-C). At least one assay mixture 194 may be formed including TRIM2 polypeptide 182, Bim polypeptide 188, and one or more of test compounds 106.

First and second luminescent tags, which also may be termed fluorescent tags, may be a transfer pair that promotes energy transfer from the first to the second luminescent tag. Energy transfer is the transfer of luminescence energy from a donor luminophore to an acceptor without emission by the donor. In energy transfer assays, a donor luminophore is excited from a ground state into an excited state by absorption of a photon. If the donor luminophore is sufficiently close to an acceptor, excited-state energy may be transferred from the donor to the acceptor, causing donor luminescence (and donor lifetime) to decrease and acceptor luminescence to increase (if the acceptor is luminescent). The efficiency of this transfer is very sensitive to the separation distance, R, between donor and acceptor, decaying as $1/R^6$. Energy transfer assays use energy transfer to monitor the proximity of donor and acceptor. Accordingly, when donor and acceptor luminescent tags are conjugated to a Bim portion and a TRIM2 portion, the energy transfer will be more efficient when the Bim and TRIM2 polypeptides are interacting with one another. In exemplary embodiments, the first and second luminescent tags may be distinct fluorescent polypeptides, such as distinct green fluorescent protein (GFP) polypeptides (e.g., cyan fluorescent protein, yellow fluorescent protein, red fluorescent protein, etc.) which may have distinct excitation and/or emission spectra. The first and second luminescent tags may be conjugated to the Bim and TRIM2 portions of their respective polypeptides at the amino terminus or the carboxy terminus of the Bim or TRIM2 portion, or may be disposed intermediate the amino and carboxy termini. In some examples, the first and second luminescent tags may have substantially nonoverlapping excitation spectra and/or emission spectra.

The spectral properties of the luminescent tags may be characterized by excitation spectrum, emission spectrum, and/or Stokes' shift, among others. An excitation spectrum is the dependence of emission intensity upon the excitation wavelength, measured at a single constant emission wavelength. An emission spectrum is the wavelength distribution of the emission, measured after excitation with a single constant excitation wavelength. A Stokes' shift is the difference in wavelengths between the maximum of the emission spectrum and the maximum of the absorption spectrum. In some examples, the emission spectrum of the first luminescent tag may overlap the excitation spectrum of the second luminescent tag, such that energy emitted from excitation of the first luminescent tag may function as (nonradiative) excitation energy for the second luminescent tag. Accordingly, by appropriate selection of excitation light, the first luminescent tag may be selectively excited directly and the second luminescent tag may be selectively excited by radiationless energy transfer.

In the present illustration, due to the presence of luminescent tags 186, 192, interaction of TRIM2 polypeptide 182 and Bim polypeptide 188 may be detected optically. For example, first luminescent tag 186 may be selectively excited using excitation light 196. Excitation energy produced by the excitation light may be transferred to second luminescent tag 192 by energy transfer. The transferred energy may excite the second luminescent tag, which may result in production of emitted light 198 from the second luminescent tag.

Optically detected signals corresponding to the amount of light emitted are indicated at 200. In the present illustration, relative to control (CONT), test compound A causes more light to be emitted (indicating more Bim-TRIM2 interaction), test compound B causes less light to be emitted (indicating less Bim-TRIM2 interaction), and test compound C has no effect on the amount of emitted light (indicating no effect on Bim-TRIM2 interaction). In other embodiments, second luminescent tag 192 may quench light emission when it is in proximity to the first luminescent tag, such that the amount of emitted light decreases with more Bim-TRIM2 interaction. Alternatively, or in addition, second luminescent tag 192 may change the fluorescence lifetime of the first luminescent tag. Accordingly, optically detected signals may measure fluorescence intensity or fluorescence lifetime, among others.

In exemplary embodiments, interaction of Bim and TRIM2 polypeptides may be detected by fluorescence resonance energy transfer (FRET) using a system generally described for other proteins in the following reference, which is incorporated herein by reference: Nguyen, A. W. and P. S. Daugherty, Evolutionary optimization of fluorescent proteins for intracellular FRET. Nat. Biotechnol., 2005. 23(3): pp. 355-360. For example, a Bim (or TRIM2) polypeptide may be tagged with YPet (a green fluorescent protein variant that is yellow) and a TRIM2 (or Bim) polypeptide may be tagged with CyPet (a green fluorescent protein variant that is blue). Each polypeptide may be tagged with YPet or CyPet by constructing a fusion polynucleotide coding sequence for each respective fusion polypeptide. For example, the polynucleotide coding sequence for YPet may be fused, in-frame, at a position corresponding to the amino terminus of Bim in a Bim polynucleotide coding sequence, to produce a YPet-Bim fusion coding sequence. In addition, the polynucleotide coding sequence for CyPet may be fused, in-frame, at a position corresponding to the amino terminus of TRIM2 in a TRIM2 polynucleotide coding sequence, to produce a CyPet-TRIM2 fusion coding sequence. YPet-Bim and CyPet-TRIM2 fusion polypeptides may be expressed from the corresponding fusion coding sequences. The fusion polypeptides may be expressed from expression vectors introduced into the same cells, to provide an optical assay performed in cells. Alternatively, or in addition, the fusion polypeptides may be isolated from the cells or expressed in a cell-free expression system, to provide an optical assay performed outside of cells.

Fluorescence polarization alternatively may provide a measure of interaction. In this case, only one of the Bim and TRIM2 polypeptides may include a luminescent tag. Fluorescence polarization signals may be detected in assay mixtures including test compounds, and the effect of the test compounds on Bim-TRIM2 interaction may be determined based on the detected signals. In particular, the extent of polarization measured from the luminescent tag may be inversely related to the amount of interaction between the Bim and TRIM2 polypeptides, because polarization will increase when the luminescent tag is part of a larger complex produced by Bim-TRIM2 interaction.

In other optical assays for interaction, the assay may detect total internal reflection luminescence (e.g., TIRF), luminescence correlation spectroscopy (e.g., FCS), and/or luminescence recovery after photobleaching (e.g., FRAP or FPR), among others.

II. Bim, TRIM2, and E2 Polypeptides

The methods, compositions, and cells disclosed herein may use and/or include at least one Bim polypeptide, at least one TRIM2 polypeptide, at least one E2 polypeptide, or any combination thereof. A "polypeptide," as used herein, is a covalently linked chain of amino acids. The chain may have any suitable number of amino acids, such as at least 10, 20, 50, or more amino acids, among others.

A Bim polypeptide, a TRIM2 polypeptide, or an E2 polypeptide, as used herein, is a polypeptide that shows substantial similarity to a respective full-length Bim, TRIM2, or E2 protein. Similarity may be determined by any suitable mechanism and may, for example, be based on the amount of sequence identity or sequence homology (amino acid identity plus conservative substitutions of amino acids) present between the polypeptide (or a subsequence thereof) and the protein. Sequence similarity may, for example, be determined by the blastp algorithm (e.g., program BLASTP 2.2.18+), as described in the following two references, which are incorporated herein by reference: Stephen F. Altschul, et al. (1997), "Gapped BLAST and PSI-BLAST: a new generation of protein database search programs," Constructs Res. 25:3389-3402; and Stephen F. Altschul et al. (2005) "Protein database searches using compositionally adjusted substitution matrices," FEBS J. 272:5101-5109. Examples of substantial similarity include at least 50%, 60%, 70%, 80%, 90%, or 95% sequence identity or homology, with optimal alignment and, if needed, introduction of gaps. Thus, a Bim, TRIM2, or E2 polypeptide that shows substantial similarity to a particular Bim, TRIM2, or E2 protein, respectively, may be identical to, related to (e.g., provided by another species of organism), and/or derived from the full-length Bim, TRIM2, or E2 protein, among others. In some embodiments, a Bim, TRIM2, or E2 polypeptide may comprise an amino acid sequence that is at least about 60%, 80%, 90%, or 95% identical and/or homologous to the amino acid sequence of a particular Bim, TRIM2, or E2 protein.

A Bim, TRIM2, or E2 polypeptide may be an engineered polypeptide, which means that the polypeptide has been designed by man to differ from a respective natural-occurring Bim, TRIM2, or E2 protein, such as by addition of one or more amino acids (e.g., a fusion polypeptide including a Bim, TRIM2, or E2 amino acid sequence plus a conjugated tag), deletion of one or more amino acids, substitution or one more amino acids, or a combination thereof. Thus, a Bim, TRIM2, or E2 polypeptide may be a fusion polypeptide that includes a foreign polypeptide sequence not found in a respective Bim, TRIM2, or E2 protein. The foreign polypeptide sequence may function as a tag, which may equip the Bim, TRIM2, or E2 polypeptide with added functionality.

A Bim, TRIM2, or E2 polypeptide may correspond most closely to, or be identical to, a respective Bim, TRIM2, and E2 protein from any suitable species. The species may, for example, be a vertebrate, such as a mammal. Exemplary mammals that may be suitable include primates (e.g., human or monkey), rodents, canines, felines, etc.

A Bim polypeptide may comprise an amino acid sequence that is at least substantially similar to a $Bim_{EL}$, $Bim_L$, $Bim_S$ protein or a combination thereof. In some embodiments, the Bim polypeptide may be more closely related to a $Bim_{EL}$ protein than to a corresponding $Bim_L$ or $Bim_S$ protein produced by alternative splicing of RNA from the same gene. $Bim_{EL}$ may interact substantially more efficiently with TRIM2 than $Bim_L$ or $Bim_S$. The Bim polypeptide may include a $Bim_{EL}$ sequence originating from one of various species of organism. For example, a Bim-TRIM2 interaction assay may be performed with a Bim polypeptide comprising an amino acid sequence with at least 60%, 80%, 90%, or 95% sequence identity or sequence homology to one or more $Bim_{EL}$ proteins, such as from human (SEQ ID NO:1 (GenBank AAC39593)); mouse (e.g., SEQ ID NO:2 (Genbank AAC40029)); rat (e.g., SEQ ID NO:3 (NCBI NP_741985)); horse (e.g., SEQ ID NO:4 (NCBI XP_001495305)); or monkey (e.g., SEQ ID NO:5 (NCBI XP_001086237)); among others. The Bim polypeptide also may include a conjugated tag, such as an epitope tag or an optical tag, which adds functionality to the polypeptide (e.g., to facilitate or enable detection) without eliminating the ability to interact with TRIM2.

A TRIM2 polypeptide may comprise an amino acid sequence that is at least substantially similar to a TRIM2 protein. The TRIM2 polypeptide may include a TRIM2 sequence originating from one of various species of organism. For example, a Bim-TRIM2 interaction assay may be performed with a TRIM2 polypeptide comprising an amino acid sequence with at least 60%, 80%, 90%, or 95% sequence identity or sequence homology to one or more TRIM2 proteins, such as from human (SEQ ID NO:6 (GenBank EAX04963); SEQ ID NO:7 (NCBI NP_001123539)); mouse (e.g., SEQ ID NO:8 (GenBank BAE24679)); rat (e.g., SEQ ID NO:9 (NCBI NP_001102022)); frog (e.g., SEQ ID NO:10 (GenBank AAH75100), SEQ ID NO:11 (GenBank AAH74184)); or fish (e.g., SEQ ID NO:12 (NCBI NP_001014393)); among others. The TRIM2 polypeptide also may include a conjugated tag, such as an epitope tag or an optical tag, which adds functionality to the polypeptide (e.g., to facilitate or enable detection) without eliminating the ability to interact with Bim. The TRIM2 protein may include a tripartite motif, namely, a RING domain, at least one B-box, and a coiled-coil region (collectively termed RBCC). Accordingly, the TRIM2 polypeptide may have any suitable combination of these motifs.

A functional equivalent to a Bim or TRIM2 polypeptide for a Bim-TRIM2 interaction assay may include only a fragment of a respective Bim or TRIM2 protein, where the fragment maintains the ability present in the full-length protein to interact with TRIM2 or Bim, respectively. The fragment may include or be only an amino terminal fragment, a carboxy terminal fragment, or an internal fragment of the respective protein. The fragment may represent any suitable portion of the respective protein, such as less or more than one-fourth or one-half, among others. Accordingly, the functional equivalent may have a subsequence of at least 25, 50, or 100 amino acids that has at least 80%, 90%, 95% or 100% amino acid identity and/or homology to a subsequence of a Bim or TRIM2 protein.

An E2 polypeptide may correspond most closely to, or be identical to, any suitable E2 ubiquitin-conjugating enzyme. Exemplary E2 enzymes that may be suitable include Ubc 1, 2, 3, 4, 5, 6, 7, 8, 10, or 13, among others.

The present disclosure also provides cells that express one or more engineered polypeptides. For example, the cells may express a Bim, a TRIM2, an E2, Bim and TRIM2, or E2 and TRIM2 engineered polypeptides. In some embodiments, the cells may express at least one engineered polypeptide (i.e., Bim, TRIM2, or E2) and may be engineered to express at least one other polypeptide (i.e., Bim, TRIM2, E2, or MAPK). The term "engineered to express," as used herein, means that cells are designed to produce the at least one other polypeptide using a polynucleotide template introduced into the cells with human intent.

Any of the Bim, TRIM2, and E2 polypeptides disclosed herein may include a tag that is attached covalently or non-covalently to a respective Bim, TRIM2, or E2 portion of the polypeptide. The term "conjugated" is intended to mean covalently attached. A tag may be conjugated translationally or postranslationally to a Bim, TRIM2, or E2 portion of a polypeptide. In exemplary embodiments, a Bim, TRIM2, or E2 polypeptide is a fusion polypeptide encoded by a recombinant coding sequence, which may be expressed in cells or in a cell-free system, among others. The tag may, for example, be an enzyme tag, that is, a tag having a measurable enzyme activity. Exemplary enzyme tags may include alkaline phosphatase, beta-galactosidase, horseradish peroxidase, etc. Alternatively, or in addition, the tag may be an affinity tag, that is, a tag that is bound by a specific binding partner, such as an antibody, biotin, a metal ion, an enzyme substrate, or the like. Exemplary affinity tags may include beta-galactosidase, $(His)_6$, glutathione S-transferase, maltose binding protein, avidin/streptavidin, or the like. Alternatively, or in addition, the tag may be an optical tag, such as a fluorescent dye and/or a fluorescent sequence of amino acids (e.g., GFP).

III. Tesr Compounds

The methods and compositions disclosed herein may use or include one or more test compounds. A "test compound," as used herein, is any chemical substance that is evaluated for activity. The test compounds may be molecules of any suitable size, such as small molecules of less than about 10 kDa. The test compounds may be evaluated individually or as one or more groups of two or more test compounds each. In some examples, the test compounds may form a set of related molecules, such as a set of polynucleotides, polypeptides, sugars, lipids, or the like. In some examples, the test compounds may be a set of polypeptides corresponding to a Bim protein, such as corresponding to distinct fragments of the Bim protein.

IV. Selecting s Test Compound as a Candidate Drug

The methods disclosed herein may involve selection of a test compound as a candidate drug based, at least in part, on an ability of the test compound to affect interaction of Bim and TRIM2 polypeptides or E2 and TRIM2 polypeptides. A test compound may be selected as a candidate drug for treating any suitable medical condition and based on any suitable effect on the interaction. For example, a test compound may be selected as a candidate drug for treating cancer based at least in part on the ability of the test compound to decrease interaction of Bim and TRIM2 polypeptides or E2 and TRIM2 polypeptides relative to control. Accordingly, the test compound may be utilized in the therapy of cancer and similar diseases where enhanced cell survival or cell resilience to chemotherapeutic agents is part of the pathology of the disease. Additional therapeutic implications may be identified in sepsis, which involves aberrant cell death signaling. Alternatively, a test compound may be selected as a candidate drug to provide a neuroprotective effect for treating a neurological disease where deregulated apoptosis (e.g., acute or prolonged periods of neurodegeneration) is a feature (e.g., stroke, Alzheimer's disease, epilepsy, Parkinson's disease, etc.) based at least in part on an ability of the test compound to increase interaction of Bim and TRIM2 polypeptides or E2 and TRIM2 polypeptides relative to control.

V. Treating Cancer Based on Testing for Bim and TRIM2 Proteins

The present disclosure provides a method of treating a patient for cancer based on analysis of the status of a Bim ubiquitination pathway in the patient. In particular, the patient may be treated if the level of Bim is low and if the Bim ubiquitination pathway is predicted to be active and thus is a potential cause of the low Bim level. By decreasing the level of Bim ubiquitination and degradation, apoptosis is promoted, thereby killing cancer cells.

One or more samples may be collected from the patient. The samples may have any suitable origin in the patient, such as a tumor, blood, urine, a fluid aspirate, or the like.

The samples may be tested for a level of a TRIM2 protein (or RNA), a Bim protein (or RNA), an active MAPK protein (or MAPK RNA), or any combination thereof. For example, the same sample may be tested for levels of two or more of the proteins (or RNAs) or at least two samples may be tested for respective distinct proteins. Testing may be performed by any suitable procedure for each protein, such as Western blot, dot blot, enzyme-linked immunosorbent assay (ELISA), competitive immunoprecipitation, mass spectrometry, or the like.

The patient may be treated with at least one drug that inhibits degradation of Bim protein if the tested levels meet predetermined criteria. In particular, the patient may be treated with the drug if selected components of the Bim ubiquitination pathway are present above or below particular thresholds. For example, the patient may be treated with the drug if the tested sample indicates that the level of Bim protein (or RNA) may be limiting for apoptosis, that is, the level of Bim protein is below a first threshold. In addition, the patient may be treated with the drug if the tested sample indicates that the low level of Bim protein may be caused in part by a relatively high level of TRIM2, that is, the level of TRIM2 protein (or RNA) is above a second threshold. Furthermore, the patient may be treated with the drug if the tested sample indicates that the low level of Bim protein may be caused in part by Bim-TRIM2 interaction promoted by Bim phosphorylation via MAPK, that is, the sample has a relatively high level of active MAPK protein (i.e., phosphorylated MAPK). In particular, the level of active MAPK protein (or MAPK RNA) is above a third threshold.

In some embodiments, a cancer patient may be treated with a Bim-stabilizing agent if Bim and TRIM2 protein levels meet one or more predefined conditions. For example, whether or not to treat the patient with the Bim-stabilizing agent may be determined by comparing the levels of Bim and TRIM2 protein to respective threshold values and/or by comparing a ratio of Bim and TRIM2 protein levels to a threshold value. In some examples, a cancer patient whose Bim and TRIM2 protein levels meet one or more predefined conditions may be treated with a combination of a Bim-stabilizing agent and a death-inducing chemotherapy agent. Further aspects of using Bim and TRIM2 protein levels to predict the efficacy of a drug combination are described below in Example 9.

Any suitable drug may be used as a Bim-stabilizing agent to inhibit Bim degradation in the patient. Exemplary drugs include a proteasome inhibitor (e.g., bortezomib, MG-132, MG-115, PSI, epoxomicin, lactacystin, etc.), a MAPK kinase (MEK) inhibitor (e.g., PD98059, U0126, SL 327, etc.), or a combination thereof.

VI. EXAMPLES

The following examples describe selected aspects and embodiments of the present disclosure, including (1) analysis of Bim protein in neuronal cultures exposed to ischemic conditions, (2) identification and confirmation of TRIM2 protein as an E3 ubiquitin ligase for Bim, (3) analysis of Bim and TRIM2 protein expression in cancer cell lines and tumors, (4) use of the Bim:TRIM2 protein ratio to predict efficacy of a drug combination, and (5) data related to interaction of TRIM2 polypeptide with E2 ubiquitin-conjugating enzymes. These examples and the various features and aspects thereof are included for illustration and are not intended to define or limit the entire scope of the present disclosure. The various features and aspects of the following examples may be combined with one another or introduced into any of the other methods or compositions of the present disclosure in any suitable combination.

Example 1

Analysis of Bim, MAPK, and Apoptosis in Neuronal Cultures

Figure 7:
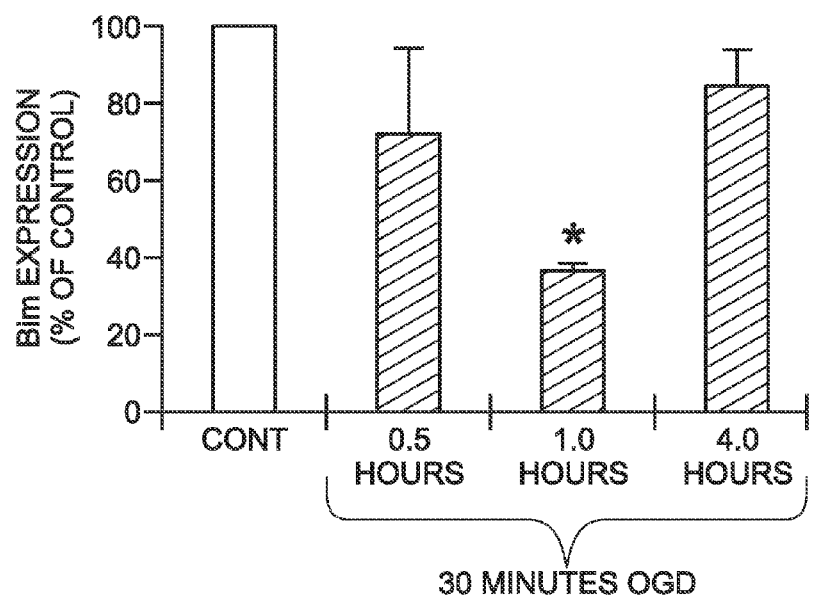
FIG. 7 is a bar graph presenting exemplary data on Bim protein levels in rat cortical neuronal cultures following preconditioning ischemia, in accordance with aspects of the present disclosure.
Figure 8:
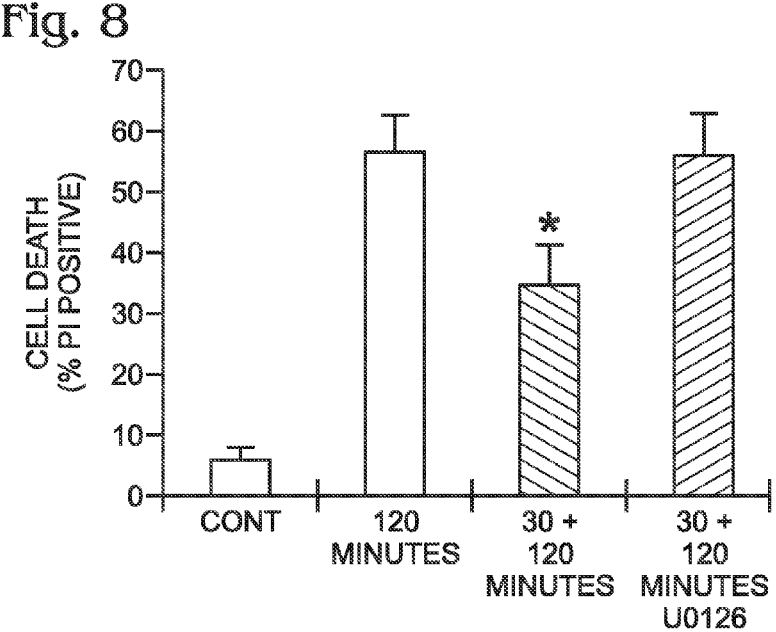
FIG. 8 is a bar graph presenting exemplary data on the percentage of dead cells produced in rat cortical neuronal cultures at 24 hours after 120 minutes of harmful ischemia (oxygen-glucose deprivation), with or without 30 minutes of preconditioning ischemia, in accordance with aspects of present disclosure.
Figure 9:
FIG. 9 is a series of immunoblots presenting exemplary data on levels of MAPK protein, phospho-MAPK protein (i.e., active MAPK protein), and Bim protein in rat cortical neuronal cultures following preconditioning ischemia, with or without a one hour recovery in the presence of the MAPK kinase (MEK) inhibitor U0126, in accordance with aspects of present disclosure.

This example describes experiments performed with cultured neurons to define the relationship between Bim degradation, short-term ischemic tolerance, and MAPK activity; see FIGS. 7-9.

Tolerance is the phenomenon whereby previous exposure to a subtoxic insult conditions a cell or organism against a more severe toxic challenge. Tolerance appears to be a conserved endogenous phenomenon and has been described in multiple organisms from simple cells to more complex systems. Ischemic tolerance has been observed in the brain; a brief preconditioning ischemic insult results in a reduced activation of cell death pathways that occur following a harmful ischemic event.

Two types of ischemic tolerance, delayed and rapid, have been reported for the brain. Delayed ischemic tolerance develops over 1-3 days in vivo or 24 h in vitro, is mediated by a gene-based mechanism, and requires new protein synthesis. In contrast, rapid ischemic tolerance is protein synthesis-independent and occurs within one hour of a preconditioning ischemia.

The experiments described in this example investigate the degradation of the pro-apoptotic Bcl-2 family member Bim as a mechanism of rapid ischemic tolerance. Bim protein levels were observed to be reduced one hour following preconditioning and occurred concurrent with an increase in Bim ubiquitination. Ubiquitinated proteins are degraded by the proteasome, and inhibition of the proteasome with MG-132 prevented Bim degradation and blocked rapid ischemic tolerance. Inhibition of p42/p44 mitogen-activated protein kinase (MAPK) activation by U0126 reduced Bim ubiquitination and Bim degradation and blocked rapid ischemic tolerance.

FIG. 7 shows a bar graph presenting exemplary data on Bim protein levels in rat cortical neuronal cultures following preconditioning ischemia. Neurons were exposed to ischemic conditions, namely, oxygen and glucose deprivation (OGD), by washing the cells with phosphate-buffered saline (NaCl (1.37 mM), KCl (2.7 mM), $Na_2HPO_4$ (10 mM), $KH_2PO_4$ (1.7 mM), pH 7.4) supplemented with 0.5 mM $CaCl_2$, 1.0 mM $MgCl_2$ and placing the cells (in culture dishes) in an anaerobic chamber (85% $N_2$, 5% $H_2$, 10% $CO_2$; 35° C.) for 30 minutes (preconditioning ischemia) or 120 minutes (harmful ischemia).

Bim protein levels were determined by immunoblotting, and then the blots were re-probed with α-tubulin to control for loading. Data were analyzed by one-way ANOVA with Bonferroni's post-hoc test. *, $p>0.05$, n=4. Bim protein levels were decreased in cortical cultures one hour following 30 min of OGD (preconditioning) but recovered to normal levels at four hours. In contrast, the expression of the pro-apoptotic cell death proteins Bid and Bax did not change (not shown).

FIG. 8 shows a bar graph presenting exemplary data on the percentage of dead cells produced in rat cortical neuronal cultures at 24 hours after 120 minutes of harmful ischemia, with (hatched bars) or without (open bars) 30 minutes of preconditioning ischemia, and with or without a one-hour recovery with U0126. Cell death was assessed 24 hours following 120 minutes of harmful ischemia using propidium iodide staining. Data shown are mean±S.E. (n=8). Data were analyzed by one-way ANOVA, with Bonferroni's post-hoc test. *, $p<0.05$.

The phosphorylation and resultant ubiquitination of Bim may be regulated by p42/p44 MAPK; hence the effect of inhibition of p42/p44 MAPK on rapid ischemic tolerance and Bim degradation was determined. Cells were incubated for one hour following 30 minutes of preconditioning OGD with either PD98059 or U0126 (both 10 μM), which are compounds that prevent p42/p44 MAPK activation by inhibiting an upstream regulatory MAPK kinase (MEK). (The upstream regulatory protein kinase MEK may activate p42/p44 MAPK via the phosphorylation of Thr202/Tyr204 residues.) Both U0126 and PD98059 (not shown) blocked the neuroprotective effect of preconditioning.

FIG. 9 shows a series of immunoblots presenting exemplary data on levels of MAPK, phospho-MAPK, and Bim protein in rat cortical neuronal cultures following preconditioning ischemia for 30 minutes, with or without a one-hour recovery in the presence of the MAPK kinase inhibitor U0126. In the top and middle panels of the figure, phosphorylation of p42/p44 MAPK was determined by immunoblot, and the blots were re-probed for total p42/p44 MAPK expression. In the bottom panel of the figure, cells were subjected to preconditioning ischemia and then recovered in the presence of U0126. Bim expression was determined by immunoblot. Data shown are representative of three independent experiments.

To show that p42/p44 MAPK activation increases following preconditioning ischemia, antibodies to phosphorylated p42/p44 MAPK were used to probe immunoblots. The level of p42/p44 MAPK phosphorylation in control cells was low; however, phosphorylation of p42/p44MAPK increased one hour following preconditioning ischemia. The increase in p42/p44 MAPK phosphorylation following preconditioning ischemia was blocked by U0126. In control cells treated with U0126 alone, there was no phosphorylation of MAPK. As a control, the same blot was probed for non-phospho-p42/p44 MAPK. Total levels of p42/p44 MAPK did not change following preconditioning ischemia or U0126 treatment. These data suggest that p42/p44 MAPK activity increased following preconditioning ischemia.

The effect of U0126 on Bim protein levels also was investigated following 30 minutes of OGD. A decrease in Bim protein expression was observed at one hour following 30 minutes of preconditioning ischemia. The decrease in Bim protein was blocked by U0126. However, U0126 had no effect on Bim protein expression in control-treated cells. These data suggest that the decrease in Bim levels observed following preconditioning is mediated via the p42/p44 MAPK system and that phosphorylation of Bim by MAPK is required for efficient Bim degradation.

Example 2

Interaction of Bim with TRIM2 from a Rat Brain Lysate

Figure 10:
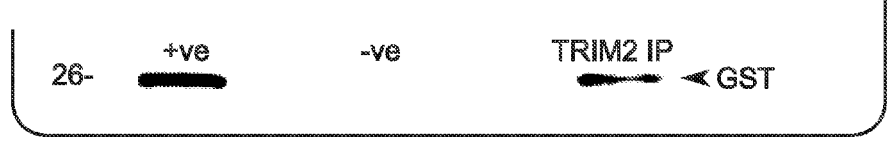
FIG. 10 is an immunoblot presenting exemplary data from interaction of Bim polypeptide with TRIM2 protein provided by a rat brain lysate, in accordance with aspects of the present disclosure.

This example describes exemplary experiments performed to identify a Bim-interacting protein in a proteomics pull-down experiment and to confirm interaction of Bim polypeptide with TRIM2 protein from a rat brain lysate; see FIG. 10.

Proteomics pull-down experiments were performed using phosphorylated GST-Bim fusion protein and cell lysates prepared from rat cortical cell cultures, in order to identify potential Bim-interacting proteins with E3-ligase potential. Bim was phosphorylated by incubating GST-Bim with active p42 (Erk2) and p44 (Erk1) MAPK (60 minutes, 37° C.). (Phosphorylation was confirmed using anti phospho-Bim (Ser55) antibody (Stressgen).) The p42/p44 MAPK was removed by immunoprecipitation and confirmed by immunoblot (not shown). Phosphorylated GST-Bim was then bound to GST beads for 30 minutes, purified, and then incubated with lysate prepared from rat cortical cells (2 mg, 1 hour, 4° C.). Samples were loaded on a 10% SDS-polyacrylamide gel and subjected to electrophoresis. Gel fragments were cut out and analyzed by mass spectrometry. Peptide sequences were subjected to homology searching using the Prophet algorithm. A peptide was deemed identified if it had a prophet score of >0.9. The mass spectrometric data identified two known Bim binding proteins, dynein and a 14-3-3 isoform (14-3-3 zeta). Only one protein (TRIM2) with an E3-ligase motif (a RING or HECT domain) was identified out of 132 potential Bim-interacting proteins.

In order to confirm interaction of Bim and TRIM2, an immunoprecipitation experiment was performed in reverse to that used to generate the mass spectrometric data. An antibody against TRIM2 was agarose-immobilized and then incubated with 500 µg of rat brain lysate and GST-Bim. Immunoprecipitated material was then resolved by electrophoresis, blotted, and probed with an anti-GST antibody (Santa Cruz). FIG. 10 shows the resulting immunoblot, which reveals that GST-Bim was immunoprecipitated from rat brain lysates using a TRIM2 antibody. As a control the TRIM2 antibody was omitted from the reaction. Therefore, TRIM2 is a Bim-interacting protein.

Example 3

Interaction of Bim and TRIM2 in a Cell-free Expression System

Figure 11:
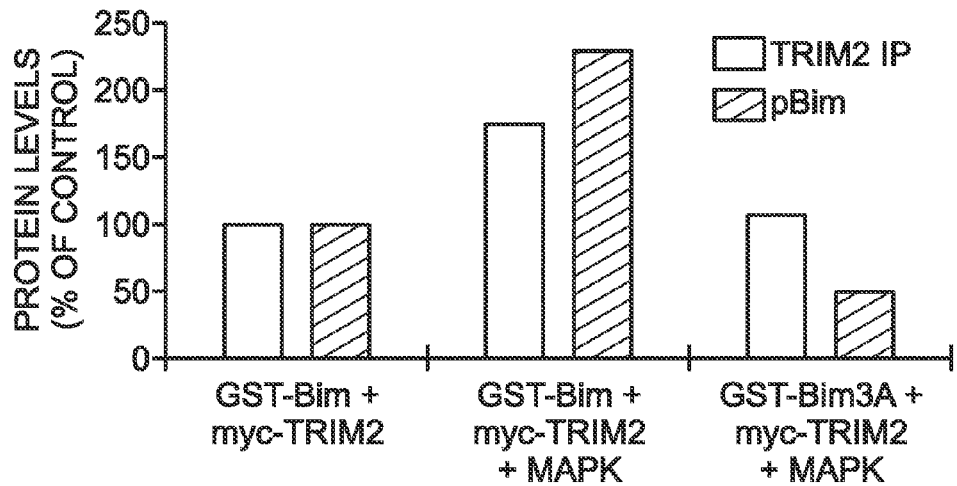
FIG. 11 is a bar graph presenting exemplary data from interaction of Bim and TRIM2 polypeptides in a cell-free expression system, in accordance with aspects of present disclosure.

This example describes exemplary data that further confirms interaction of Bim and TRIM2 using a cell-free expression system; see FIG. 11.

An in vitro transcription-translation assay was employed to further confirm the binding of TRIM2 to Bim. Myc-tagged TRIM2 (myc-TRIM2) was synthesized by in vitro transcription of cDNA clones (pGBKT7-TRIM2) using T7 RNA polymerase, followed by in vitro translation in a nuclease-treated rabbit reticulocyte lysate system (Promega). Expression of myc-TRIM2 polypeptide was confirmed by immunoblot, which identified an 80 kDa polypeptide corresponding to a TRIM2 protein. Incubation of TRIM2 polypeptide with Bim resulted in low levels of Bim ubiquitination, however addition of active MAPK to the reaction enhanced Bim ubiquitination. Bim ubiquitination was present without adding MAPK, which may be due to high basal levels of active MAPK in the reticulocyte lysate supernatant.

To confirm further that Bim and TRIM2 interact, the translated myc-TRIM2 polypeptide was incubated with GST-Bim polypeptide (Millipore). Polypeptides were separated by GST immunoprecipitation and TRIM2 binding was determined by c-myc immunoblotting of immunoprecipitated proteins using an anti-c-myc antibody or with a phospho-specific Bim antibody against phosphor-Ser 65 of Bim. The results are quantified in FIG. 11. TRIM2 was immunoprecipitated much more efficiently when active p42/p44 MAPK (Millipore) was added to the reaction. To show that the precipitation was specific for phosphorylated Bim, TRIM2 also was incubated with the non-phosphorylatable mutant, GST-Bim3A. Precipitation of myc-TRIM2 with GST-Bim3A in the presence of MAPK was not observed. These data show that the binding of Bim protein to TRIM2 protein may require phosphorylation of Bim protein by p42/p44 MAPK on Ser 55, 65, 73, or a combination thereof.

Example 4

Interaction of Bim and TRIM2 in a MEF Cell Line

Figure 12:
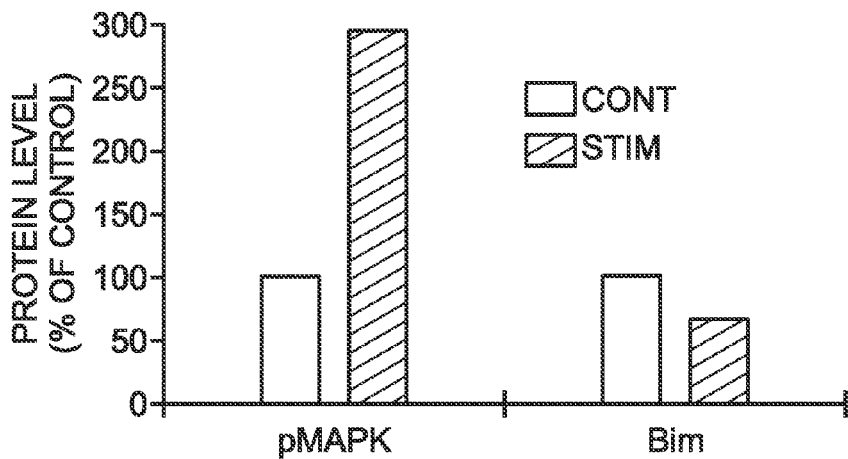
FIG. 12 is a bar graph presenting exemplary data on levels of phospho-MAPK protein and Bim protein in a mouse embryonic fibroblast cell line, in accordance with aspects of present disclosure.
Figure 13:
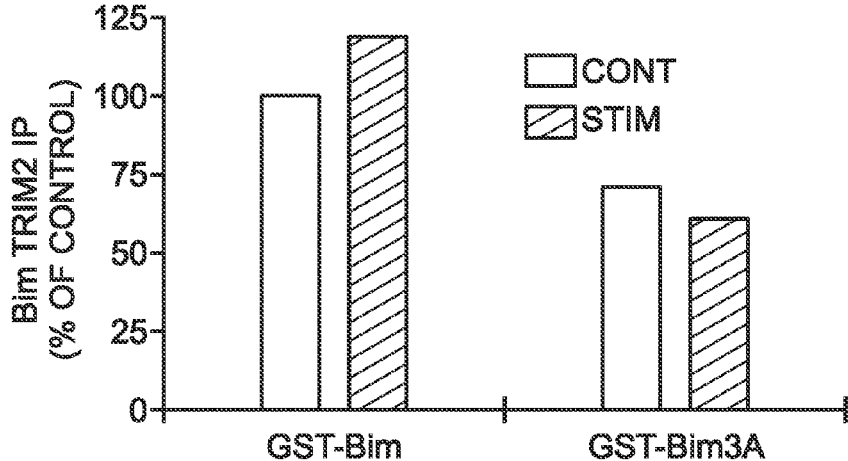
FIG. 13 is a bar graph presenting exemplary data on interaction of a Bim polypeptide with TRIM2 protein from a mouse embryonic fibroblast cell line, in accordance with aspects of present disclosure.

This example describes exemplary experiments demonstrating interaction of Bim and TRIM2 in a mouse embryonic fibroblast (MEF) cell line; see FIGS. 12 and 13.

Bim ubiquitination that is dependent on p42/p44 MAPK was originally described in the MEF cell line. To confirm that TRIM2 protein mediates Bim ubiquitination in the MEF cell line, cells were subjected to overnight serum starvation and then were stimulated with serum for one hour ("STIM"), which enhances Bim ubiquitination and degradation. Bim protein and phospho p42/p44 MAPK levels then were determined by immunoblot (FIG. 12). Compared to control ("CONT"), both an increase in MAPK phosphorylation and a decrease in Bim protein levels were observed in these cells following stimulation.

FIG. 13 shows quantified results from co-immunoprecipitation experiments analyzed by immunoblot with anti-GST antibody. MEF cell lysates were incubated with GST-Bim, and then were subjected to immunoprecipitation with anti-TRIM2 antibody.

GST-Bim was observed to co-immunoprecipitate with TRIM2 protein from stimulated cell lysates, but not from unstimulated cell lysates. When MEF cell lysates were incubated with a nonphosphorylatable Bim mutant (GST-Bim3A), an increase in Bim immunoprecipitation was not observed with stimulation. These data show that in a cell line with well-characterized Bim ubiquitination, TRIM2 interacts with Bim in a MAPK-dependent manner.

Example 5

Interaction of Bim and TRIM2 in Neuronal Cultures with Ischemia

Figure 14:
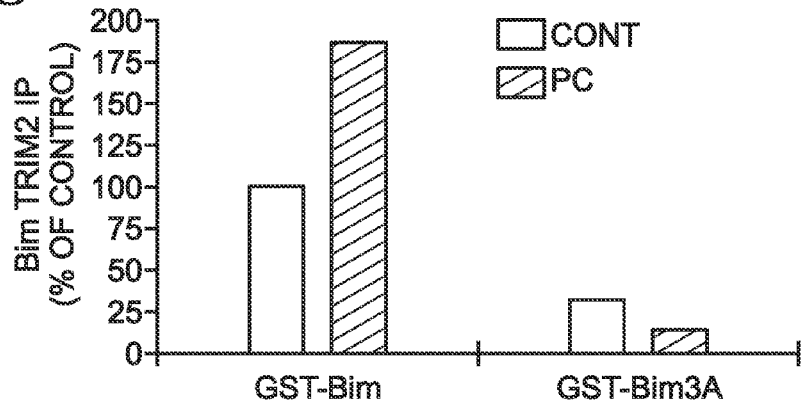
FIG. 14 is a bar graph presenting exemplary data on interaction of a Bim polypeptide with TRIM2 protein under conditions that promote Bim ubiquitination in rat cortical neuronal cultures, in accordance with aspects of present disclosure.
Figure 15:
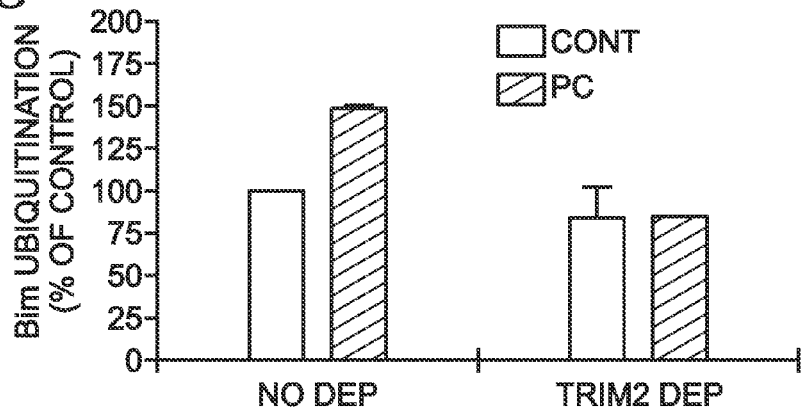
FIG. 15 is a bar graph presenting exemplary data on ubiquitination of Bim protein in neuronal cell lysates with and without TRIM2 depletion using an anti-TRIM2 antibody, in accordance with aspects of present disclosure.

This example describes exemplary experiments demonstrating p42/p44 MAPK-dependent Bim and TRIM2 interaction under conditions that promote Bim ubiquitination in neurons; see FIGS. 14 and 15.

Preconditioning ischemia in cortical neurons was found to reduce Bim protein levels to less than 50% of control values (see Example 1). To follow up on this observation, co-immunoprecipitation was utilized to determine whether TRIM2 binding to Bim correlates with the degradation of Bim following preconditioning ischemia in neuronal cultures. GST-Bim was incubated with cell lysates from control neurons ("CONT"; open bars) and neurons exposed to preconditioning ischemia ("PC"; hatched bars). GST-Bim interacting with TRIM2 then was co-immunoprecipitated with anti-TRIM 2 antibody and detected by immunoblot with an anti-GST antibody.

FIG. 14 shows the results presented as a bar graph. Interaction of GST-Bim polypeptide with TRIM2 protein was found to be low in control cells, but increased one hour after a 30-minute period of preconditioning ischemia. Co-immunoprecipitation of Bim was not observed when lysates were incubated with a non-phosphorylatable Bim mutant, GST-Bim3A. Furthermore, co-immunoprecipitation of GST-Bim polypeptide with TRIM2 protein was reduced when cells were incubated with the MAPK kinase inhibitor U0126, which blocks Bim degradation and rapid ischemic tolerance (see Example 1 and data not shown).

FIG. 15 shows a bar graph presenting exemplary data on Bim ubiquitination in neuronal cell lysates. Ubiquitination of GST-Bim polypeptide was conducted by incubating this fusion protein in neuronal cell lysates, either with ("TRIM2 DEP") or without ("NO DEP") prior depletion of TRIM2 protein using an anti-TRIM2 antibody, and with lysates prepared from preconditioned neuronal cultures ("PC"; hatched bars) or control neuronal cultures ("CONT"; open bars). Bim ubiquitination was measured by immunoprecipitating GST-Bim from the lysates and then probing an immunoblot of immunoprecipitated GST-Bim for ubiquitin using an anti-ubiquitin antibody. The bar graph of FIG. 15 shows that immunodepletion of TRIM2 protein reduces Bim ubiquitination in lysates from preconditioned cells to that of control lysates. Taken together, these data confirm that under conditions where Bim ubiquitination increases, Bim binds to TRIM2 and removal of TRIM2 from cell lysates prevents Bim ubiquitination in an ex vivo assay following preconditioning ischemia.

Example 6

RNA Interference of TRIM2 Expression in Neurons

Figure 16:
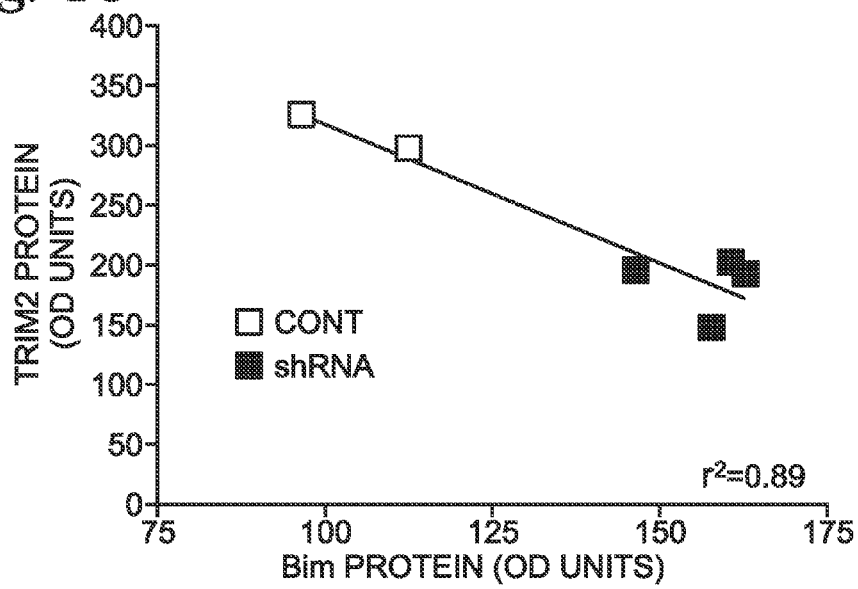
FIG. 16 is a graph presenting exemplary data on TRIM2 and Bim protein levels in neurons, with and without interference with TRIM2 expression using a short hairpin RNA, in accordance with aspects of present disclosure.

This example describes exemplary experiments demonstrating an inverse relationship between Bim and TRIM2 protein levels using knockdown of TRIM2 with a short hairpin RNA (shRNA); see FIG. 16.

If TRIM2 is the primary E3 ligase for Bim in cortical neurons, reduction of TRIM2 protein should increase Bim protein stability and thus the steady state level of Bim protein. In order to test this idea, shRNA directed to TRIM2 mRNA was employed to reduce TRIM2 protein expression.

FIG. 16 is a graph presenting exemplary data on TRIM2 and Bim protein levels in cortical neurons, with ("shRNA") and without ("CONT") RNA interference of TRIM2 protein expression. A lentivirus system was used to deliver a TRIM2 shRNA expression vector to the neurons by incubation with the neurons for 72 hours. TRIM2 and Bim protein levels were determined by immunoblot and are plotted in FIG. 16. Exposure of the neurons to TRIM2 shRNA resulted in a 40% decrease in TRIM2 protein levels. The shRNA produced only a modest decrease in TRIM2 expression, which may be explained by the relatively long half-life measured for TRIM2 protein, namely, a half-life exceeding 24 hours (not shown). Significantly, treatment with TRIM2 shRNA also produced a change in the ratio of TRIM2 to Bim protein, namely, a corresponding 40% increase in Bim protein levels in the same neurons, which is an inverse relationship and is consistent with TRIM2 protein functioning as a Bim E3-ligase.

Example 7

Bim:TRIM2 Expression Ratios in Breast Cancer Cell Lines

This example describes exemplary experiments suggesting a role of TRIM2 in regulating Bim degradation in breast tumor cells; see FIG. 17.

Intracellular mechanisms preventing apoptosis are frequently implicated in oncogenesis. While Bcl-2 is protective in ischemia, it may be harmful in cancer. Therefore, experiments were performed to determine whether TRIM2 overexpression and Bim degradation could play a role in breast cancer.

FIG. 17 shows a graph presenting exemplary data on Bim:TRIM2 protein ratios in established breast cancer cell lines. High levels of TRIM2 protein and low levels of Bim protein were observed in the breast tumor cell line HCC1419. In contrast, MCF-7 cells showed higher levels of Bim protein and lower levels of TRIM2 protein. Interestingly, HCC1419 cells overexpress HER2, whereas MCF-7 cells do not.

Example 8

Expression of TRIM2 and Bim in Breast Tumor Samples

Figure 19:
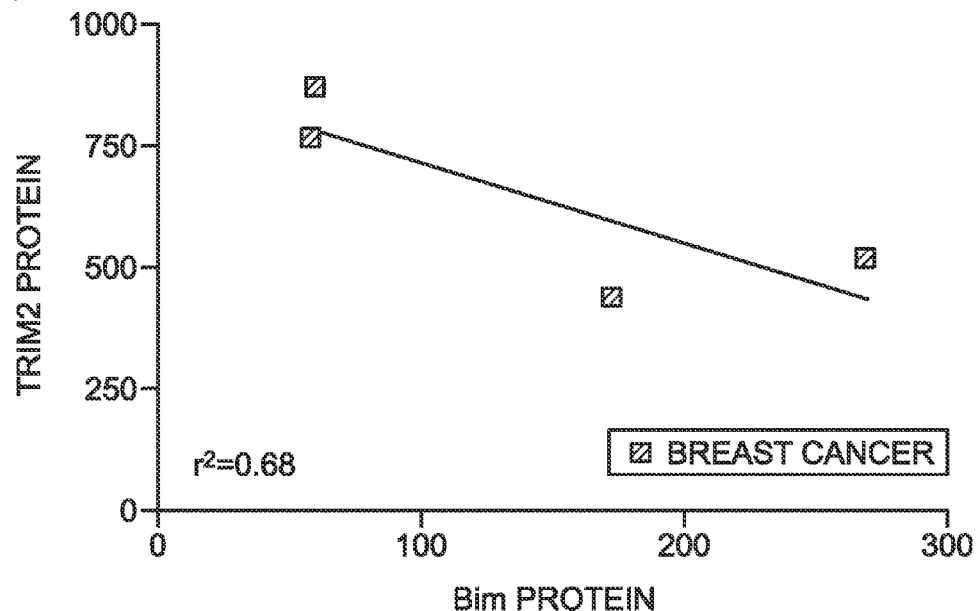
FIG. 19 is a graph of the expression data of FIG. 18.

This example describes exemplary experiments analyzing expression of TRIM2 protein in primary breast tumors; see FIGS. 18 and 19.

FIG. 18 shows a pair of immunoblots presenting exemplary data on expression of TRIM2 and Bim protein in breast tumor samples, and FIG. 19 is a graph of the expression data of FIG. 18. Four samples of breast tissue were obtained during surgery to remove breast tumors. The samples were tested for Bim and TRIM2 protein expression levels using immunoblot. As shown in the figures, Bim and TRIM2 levels appear to be reciprocally regulated in these samples. Interestingly, samples 1 and 3, which are from patients with HER2/neu-positive tumors, show high levels of TRIM2. Samples 2 and 4, which were not overexpressing HER2/neu, showed lower TRIM2 levels and higher Bim levels. The expression of TRIM2 is unrelated to drug treatment, because all of these patients were untreated prior to surgery. These results suggest that Bim and TRIM2 protein expression may be altered in certain cancer types and particularly that TRIM2 protein expression may be elevated in HER2/neu-positive, drug-naive tumors.

Additional experiments demonstrated that TRIM2 is upregulated in other cancer types. Bim and TRIM2 appear reciprocally regulated in lung, muscle, and sarcoma tumor samples. This suggests that TRIM2 may play a role in tumor resilience to cell death in other types of cancer.

Example 9

The Bim:TRIM2 Ratio as a Predictor of Drug Combination Efficacy

Figure 21:
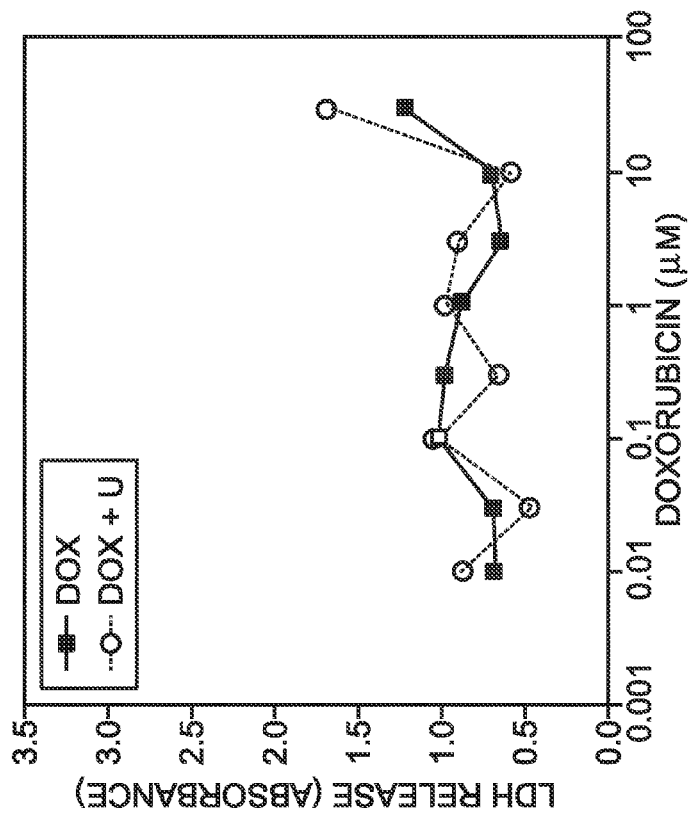
FIG. 21 is a graph plotting exemplary LDH release data obtained with MCF-7 cells, a breast cancer cell line with a high Bim:TRIM2 ratio, as a function of doxorubicin concentration and the presence/absence of U0126, in accordance with aspects of present disclosure.
Figure 20:
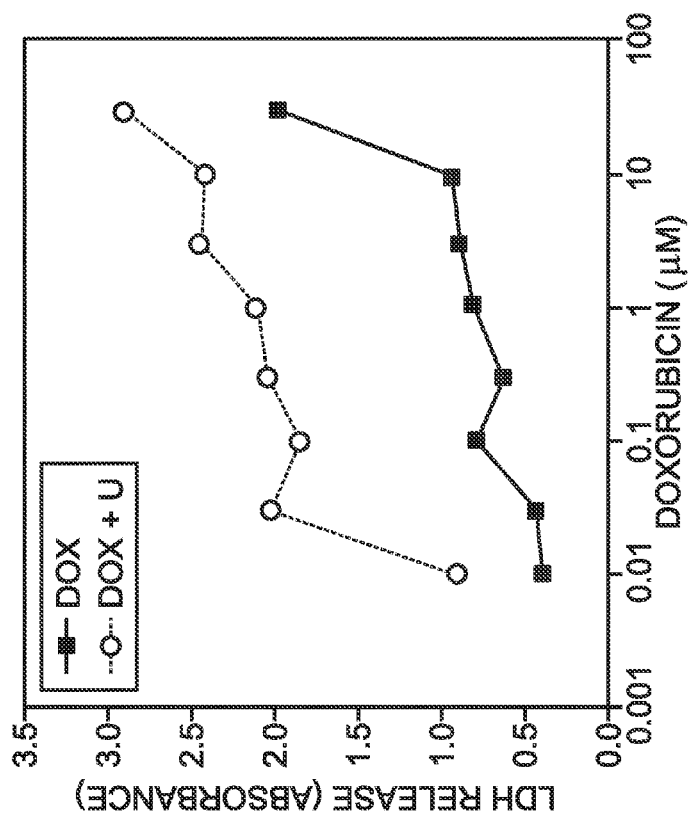
FIG. 20 is a graph plotting exemplary LDH release data obtained with HCC1419 cells, a breast cancer cell line with a low Bim:TRIM2 ratio, as a function of doxorubicin concentration and the presence/absence of U0126, in accordance with aspects of present disclosure.

This example describes exemplary experiments demonstrating the use of observed Bim:TRIM2 protein ratios to predict sensitivity to a combination of a cell-death inducing agent, such as doxorubicin, and an inhibitor of Bim degradation; see FIGS. 20 and 21.

The stabilization of Bim in cells by blocking Bim degradation may sensitize the cells to an additional anti-cancer agent and promote cell death. To test this hypothesis, breast cancer cell lines with low and high Bim:TRIM2 protein ratios, HCC1419 and MCF-7, respectively (see FIG. 17), were compared for sensitivity to doxorubicin alone ("DOX") or in combination with an inhibitor of Bim degradation, namely, U0126 ("DOX+U"). Incubation of HCC1419 cells with U0126 alone, which stabilizes Bim, does not induce cell death. Cell death was measured as a release of the enzyme lactate dehydrogenase (LDH), which is detected as absorbance at 492 nm. However, an effect of combining a Bim-stabilizing agent with doxorubicin is predicted by the low Bim:TRIM2 protein ratio in HCC1419 cells.

Cells were incubated with various concentrations of doxorubicin (μM) for 72 h, in the absence (solid squares) or presence (open circles) of 100 μM U0126. FIG. 20 shows a leftward shift in the response of HCC1419 cells to doxorubicin when U0126 is present. The calculated $EC_{50}$ of doxorubicin alone was 60 μM in these cells versus 0.01 μM when combined with U0126. Therefore, doxorubicin, when combined with U0126, may be used effectively at a much lower concentration in some cancer patients, which may reduce undesirable damage caused by doxorubicin chemotherapy, such as cardiotoxicity. In contrast to the data of FIG. 20, FIG. 21 shows that MCF-7 cells exhibited no increased responsiveness to a combination of doxorubicin and U0126 relative to doxorubicin alone. Accordingly, blocking MEK using U0126 results in an enhancement of doxorubicin-induced cell death in HCC1419 cells, a cell line with a low Bim:TRIM2 ratio, but this effect is not observed in MCF-7 cells, which have a high Bim:TRIM2 ratio. Thus, a ratio of levels of TRIM2 and Bim proteins may act as a biomarker to predict response to a rationally-designed combination therapy, which utilizes a Bim stabilizing agent with a cell death-inducing agent.

The observations of this example provide a method of treating cancer. At least one sample from a cancer patient may be tested for a level of Bim protein and a level of TRIM2 protein. The Bim protein may have at least about 95% identity to SEQ ID NO:1, and the TRIM2 protein may have at least about 95% identity to one or both of SEQ ID NO:6 and SEQ ID NO:7. The sample may, for example, be blood, urine, saliva, a tissue biopsy, a fluid aspirate, a combination thereof, or the like. The sample may include cancer cells, such as cancer cells from a solid tumor, lymph nodes, blood, or the like. The Bim and TRIM2 protein levels may be measured using any suitable methodology, either with or without extraction of protein from cells. Exemplary approaches for testing Bim and TRIM2 levels may include ELISA, Western blot, or cell imaging assays, among others. A determination may be made whether or not to treat the cancer patient with a combination of (a) a Bim degradation inhibitor (also termed a Bim-stabilizing agent) and (b) a toxic chemotherapeutic agent (i.e., a cell death-inducing agent), based on a ratio of the levels of Bim and TRIM2 protein. For example, the combination may be used for treatment if the ratio of Bim:TRIM2 is low (i.e., the ratio of TRIM2 to Bim is high enough to exceed a threshold value). The Bim degradation inhibitor may be an inhibitor of MAP kinase, such as apigenin (4',5,7-trihydroxyflavone), PD 169316, SB202190, SB203580; an inhibitor of MAP kinase kinase (MEK), such as PD98059, U0126, SL 327, etc.; a proteasome inhibitor (e.g., bortezomib, MG-132, MG-115, PSI, epoxomicin, lactacystin, etc.); a direct inhibitor of Bim-TRIM2 interaction; or a combination thereof, among others. The cell-death inducing agent may, for example, be any chemotherapy agent used to kill cancer cells. Exemplary cell-death inducing agents may include at least one DNA-targeting agent, such as a DNA-intercalating agent (e.g., doxorubicin or cisplatin), a DNA-alkylating agent (e.g., cyclophosphamide), or a combination thereof, among others.

Example 10

Interaction of TRIM2 with E2 Ubiquitin-conjugating Enzymes

Figure 22:
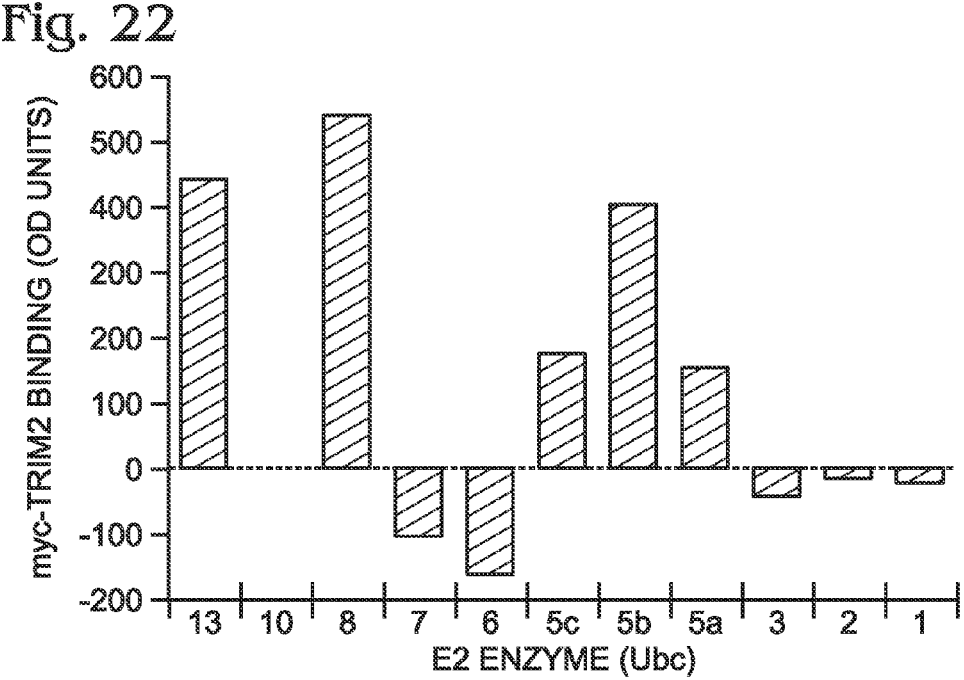
FIG. 22 is a bar graph presenting exemplary data on interaction of TRIM2 with various E2 ubiquitin-conjugating enzymes, in accordance with aspects of present disclosure.

This example describes exemplary experiments demonstrating interaction of TRIM2 with E2 ubiquitin-conjugating enzymes; see FIG. 22.

FIG. 22 show a bar graph presenting exemplary data on interaction of TRIM2 polypeptide with various E2 ubiquitin-conjugating enzymes. E2 ubiquitin-conjugating enzymes supply the ubiquitin to the E3-ligase for conjugation to a target protein. To test interaction of TRIM2 polypeptide with E2 enzymes, a set of E2 enzymes, namely, Ubc 1, 2, 3, 5a, 5b, 5c, 6, 7, 8, 10, and 13, were loaded onto a gel and transferred onto a PVDF membrane. The immobilized proteins were incubated with E1 enzyme, ubiquitin, and ATP for 10 min, and then with c-myc-TRIM2, GST-Bim and active ERK1/2 (MAPK) for 20 min at room temperature. The membrane was washed, probed with anti-c-myc antibody, exposed, and quantified. The results are present in graphical form in FIG. 22. TRIM2 was bound to Ubc 5a, 5b, 5c, 8, and 13 which suggests that these E2 enzymes can supply the ubiquitin to TRIM2 for ubiquitination of target proteins.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A method of drug screening, comprising:
forming a plurality of assay mixtures each including a Bim polypeptide, a TRIM2 polypeptide, and at least one test compound, wherein the Bim polypeptide comprises an amino acid sequence with at least about 80% homology to one or more of SEQ ID NOS:1-5, wherein the TRIM2 polypeptide comprises an amino acid sequence with at least about 80% homology to one or more of SEQ ID NOS:6-12, and wherein at least one of the Bim and TRIM2 polypeptides comprises a fluorescent tag;
detecting fluorescence signals from the fluorescent tag representing interaction of the Bim and TRIM2 polypeptides with each other; and
determining based on the signals whether the at least one test compound in each assay mixture affected the ability of the Bim and TRIM2 polypeptides to interact.

2. The method of claim 1, wherein the step of detecting fluorescence signals includes a step of detecting fluorescence resonance energy transfer or fluorescence polarization.

3. The method of claim 1, wherein each of the Bim and TRIM2 polypeptides comprises a fluorescent tag.

4. The method of claim 1, wherein the step of forming a plurality of assay mixtures disposes an antibody in each assay mixture, and wherein the antibody is configured to bind to the Bim polypeptide or the TRIM2 polypeptide.

5. The method of claim 4, wherein at least one of the Bim and TRIM2 polypeptides comprises a conjugated epitope tag.

6. The method of claim 1, wherein the step of forming a plurality of assay mixtures includes a step of forming a plurality of assay mixtures that each include a MAP kinase enzyme.

7. The method of claim 6, wherein the step of forming a plurality of assay mixtures includes a step of forming a plurality of assay mixtures that each include a MAP kinase kinase (MEK) enzyme.

8. The method of claim 7, wherein the step of forming a plurality of assay mixtures includes a step of disposing an inhibitor of MAP kinase function in at least one of the assay mixtures.

9. The method of claim 1, wherein the step of detecting fluorescence signals is performed with the plurality of assay mixtures disposed in wells of a microplate.

10. The method of claim 1, wherein the assay mixtures include biological cells that express the Bim and TRIM2 polypeptides.

11. A method of drug screening, comprising:
   forming a plurality of assay mixtures each including a Bim polypeptide, a TRIM2polypeptide, and at least one test compound, wherein the Bim polypeptide comprises an amino acid sequence with at least about 80% sequence homology to one or more of SEQ ID NOS:1-5, wherein the TRIM2 polypeptide comprises an amino acid sequence with at least about 80% sequence homology to one or more of SEQ ID NOS:6-12, and wherein at least one of the Bim and TRIM2 polypeptides is attached to a tag;
   detecting signals generated by the tag and indicating a level of association of the Bim and TRIM2 polypeptides with each other; and
   determining based on the signals whether the at least one test compound in each assay mixture affected the ability of the Bim and TRIM2 polypeptides to associate with each other.

12. The method of claim 11, wherein the tag is attached covalently to one of the Bim and TRIM2 polypeptides.

13. The method of claim 11, wherein the tag is an epitope tag, further comprising a step of including in each of the assay mixtures an antibody that binds the epitope tag.

14. The method of claim 11, wherein the assay mixtures include biological cells that express the Bim and TRIM2 polypeptides.

* * * * *